US009811632B2

(12) United States Patent
Grabiner et al.

(10) Patent No.: US 9,811,632 B2
(45) Date of Patent: *Nov. 7, 2017

(54) COMPUTING SYSTEMS AND METHODS FOR ELECTRONICALLY INDICATING THE ACCEPTABILITY OF A PRODUCT

(71) Applicant: TEMPTIME CORPORATION, Morris Plains, NJ (US)

(72) Inventors: Frederick Robert Grabiner, Livingston, NJ (US); Carl Michael Lentz, Cedar Knolls, NJ (US); Emily Moore, Haddam Neck, CT (US); Thaddeus Prusik, Stroudsburg, PA (US); Nicholas Puro, Briarcliff Manor, NJ (US); Bruce-Erik Osborn, West Vancouver (CA)

(73) Assignee: TEMPTIME CORPORATION, Morris Plains, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 14/981,457

(22) Filed: Dec. 28, 2015

(65) Prior Publication Data
US 2016/0154939 A1 Jun. 2, 2016

Related U.S. Application Data

(60) Division of application No. 13/276,543, filed on Oct. 19, 2011, now Pat. No. 9,224,120, which is a
(Continued)

(51) Int. Cl.
G06Q 99/00 (2006.01)
G06F 19/00 (2011.01)
(Continued)

(52) U.S. Cl.
CPC .......... *G06F 19/327* (2013.01); *G06F 19/321* (2013.01); *G06K 9/4652* (2013.01);
(Continued)

(58) Field of Classification Search
CPC ........ G06T 2207/30128; G06Q 10/083; G06Q 10/0635; G06Q 10/087
(Continued)

(56) References Cited

U.S. PATENT DOCUMENTS 4,917,503 A 4/1990 Bhattacharjee
5,057,434 A 10/1991 Prusik et al.
(Continued)

FOREIGN PATENT DOCUMENTS

EP 0 117 390 9/1984
WO WO 2007114976 10/2007
(Continued)

OTHER PUBLICATIONS

"Security Inks", International Paper Knowledge Center, downloaded Mar. 11, 2010.
(Continued)

Primary Examiner — Kira Nguyen
(74) Attorney, Agent, or Firm — K&L Gates LLP

(57) ABSTRACT

In part, the invention relates to computing systems and methods for electronically indicating the acceptability of a product. An image capture and communication device may analyze a product label that includes one or more monitors, authentication elements, and identification elements. The image capture and communication device may determine the type and features of the monitors, authentication elements, and identification elements. The image capture and communication device may transmit data based on the type and features to a host server, which may transmit data associated with the host product to the image capture and communi-
(Continued)

cation device in, inter alia, the form of an acceptability report.

20 Claims, 18 Drawing Sheets

Related U.S. Application Data continuation-in-part of application No. 12/799,252, filed on Apr. 20, 2010, now Pat. No. 9,053,616.

(51) Int. Cl.
| | |
|---|---|
| *G06Q 10/08* | (2012.01) |
| *G07G 1/00* | (2006.01) |
| *G06Q 30/06* | (2012.01) |
| *G06K 9/46* | (2006.01) |
| *G06K 9/62* | (2006.01) |
| *G06T 7/73* | (2017.01) |
| *G06T 7/90* | (2017.01) |

(52) U.S. Cl.
CPC ......... *G06K 9/6215* (2013.01); *G06Q 10/087* (2013.01); *G06Q 10/0833* (2013.01); *G06Q 30/0623* (2013.01); *G06T 7/73* (2017.01); *G06T 7/90* (2017.01); *G07G 1/0054* (2013.01); *G07G 1/0081* (2013.01); *G06F 19/3462* (2013.01); *G06F 19/3475* (2013.01); *G06K 2009/4666* (2013.01)

(58) Field of Classification Search
USPC .......................................... 705/317; 382/141
See application file for complete search history.

(56) References Cited

U.S. PATENT DOCUMENTS

| | | | |
|---|---|---|---|
| 5,744,786 A | 4/1998 | Kim | |
| 6,119,932 A | 9/2000 | Maloney et al. | |
| 6,544,925 B1 | 4/2003 | Prusik et al. | |
| 6,640,002 B1 * | 10/2003 | Kawada | G06T 7/70 348/87 |
| 7,209,042 B2 | 4/2007 | Martin et al. | |
| 7,430,588 B2 | 9/2008 | Hunter | |
| 7,490,575 B2 | 2/2009 | Taylor et al. | |
| 7,562,811 B2 | 7/2009 | Nemet et al. | |
| 7,571,695 B2 | 8/2009 | Taylor et al. | |
| 7,809,152 B2 | 10/2010 | Zhao et al. | |
| 8,086,023 B2 * | 12/2011 | Shimodaira | G06K 9/6204 382/149 |
| 8,091,776 B2 | 1/2012 | Nemet et al. | |
| 8,196,821 B2 | 6/2012 | Nemet et al. | |
| 8,757,503 B2 | 6/2014 | Conzelmann | |
| 2003/0165602 A1 | 9/2003 | Garwood | |
| 2003/0216969 A1 | 11/2003 | Bauer et al. | |
| 2005/0011957 A1 | 1/2005 | Attia et al. | |
| 2005/0198095 A1 | 9/2005 | Du et al. | |
| 2006/0034602 A1 | 2/2006 | Fukui | |
| 2006/0157559 A1 | 7/2006 | Levy et al. | |
| 2006/0200480 A1 | 9/2006 | Harris et al. | |
| 2007/0012784 A1 | 1/2007 | Mercolino | |
| 2007/0160814 A1 | 7/2007 | Mercolino | |
| 2007/0235528 A1 | 10/2007 | Spencer et al. | |
| 2007/0274561 A1 | 11/2007 | Rhoads et al. | |
| 2008/0156876 A1 | 7/2008 | Vinogradov | |
| 2008/0298472 A1 | 12/2008 | Jain et al. | |
| 2009/0063307 A1 | 3/2009 | Groenovelt et al. | |
| 2009/0207881 A1 | 8/2009 | Nakatani | |
| 2009/0244630 A1 | 10/2009 | Miyazaki | |
| 2009/0327258 A1 | 12/2009 | Lou et al. | |
| 2010/0051707 A1 | 3/2010 | Conzelmann | |
| 2010/0119158 A1 | 5/2010 | Dalal et al. | |
| 2010/0141756 A1 | 6/2010 | Grote et al. | |
| 2010/0219235 A1 | 9/2010 | Nemet et al. | |
| 2010/0293106 A1 | 11/2010 | Rhoads et al. | |
| 2010/0327051 A1 | 12/2010 | Lyon et al. | |
| 2011/0006109 A1 | 1/2011 | Nemet et al. | |
| 2011/0006115 A1 | 1/2011 | Nemet et al. | |
| 2011/0050872 A1 | 3/2011 | Harbert et al. | |
| 2011/0258130 A1 | 10/2011 | Grabiner et al. | |

FOREIGN PATENT DOCUMENTS

| | | |
|---|---|---|
| WO | WO 2010112674 | 10/2010 |
| WO | WO 2011057695 | 5/2011 |

OTHER PUBLICATIONS

European Search Report issued in EP12842082.5 dated May 11, 2015. 7 pages.
PCT Search Report and Written Opinion dated Jan. 9, 2013 issued for International PCT Application No. PCT/US12/58699.
The International Search Report and Written Opinion issued for International Application No. PCT/US2011/001158, dated Nov. 3, 2011.
Covectra. Multi-Layered Brand Protection. Unit Level Serialization and Mobile/Smartphone Authentication, presentation given by Steve Wood, President of Covectra at the 5th Glo.
PharmaSecure. Product Security, Branding, and Marketing for Emerging Markets, presentation material at 5th Global Forum on Pharmaceutical Anti-counterfeiting, Feb. 2010.
Brand Protection and Market Intelligence for Cash-Based Societies, Sproxil, presentation material at 5th Global Forum on Pharmaceutical Anti-counterfeiting, Feb. 2010.
Consortium Reports Successful Drug Tracking and Authenticating Pilot, by daphne, PMPNews.com, Mar. 5, 2010, downloaded on Jul. 30, 2012.
Basta, "Brand Protection Technology Takes a Patient-Communication Turn", PC Pharmaceutical Commerce, Mar. 3, 2010, downloaded on Jul. 30, 2012.
Healthcare & Life Sciences. Pharmaceuticals & Medical Devices, resentation material at 5th Global Forum on Pharmaceutical Anti-counterfeiting, Feb. 2010.
Mc-Graw-Hill Book Company, McGraw-Hill Yearbook of Science & Technology, 1987, pp. 205-206.
Zall, et al., "Evaluation of Automated Time Temperature Monitoring System in Measuring Freshness of UHT Milk", Dairy and Food Sanitation, vol. 6, No. 7 (Jul. 1986); pp. 285-29.
Anonymous, "Smart labels: tracking products and freshness", Modern Material Handling, 1986, pp. 2-5.
Fields et al., "Shelf life estimation of beverage and food products using bar coded time-temperature indicator labels", The Shelf Life of Food and Beverages, 1986, p. 23.
Lifelines, Computerizing Shelf Life Analysis, Product Information, 1989.
Teskey, M., "Turning RFID Data into Information", 2008, downloaded Feb. 23, 2010.
Apple—iPhone—Technical Specifications, downloaded on Mar. 31, 2010.
"Will Serialization Make Authentication Obsolete?", 5th Global Forum on Pharmaceutical AntiCounterfeiting, Feb. 2010, Miami, Florida, presented by Jim Rittenburg.
"Barcode", downloaded from Wikipedia on Feb. 22, 2010.
Van Arnum, P., "Epedigree in the Pharmaceutical Supply Chain", 2008, downloaded on Feb. 23, 2010.
iPhone User Guide, for iPhone OS 3.1 Software. Apple, Inc. (2009).

* cited by examiner

Product may be used.

Product Authenticity: ✓ OK
Temperature Monitor: ✓ OK
Product Expiration: ✓ OK

FIG. 2E

Temperature Monitor Expired.
*Do Not Use Product*

Product Authenticity: ✓ OK
Temperature Monitor: ✗
Product Expiration: ✓ OK

FIG. 2F

COMPUTING SYSTEMS AND METHODS FOR ELECTRONICALLY INDICATING THE ACCEPTABILITY OF A PRODUCT

CROSS REFERENCE TO RELATED APPLICATIONS

The present application is a divisional application of U.S. patent application Ser. No. 13/276,543, filed on Oct. 19, 2011, which is a continuation-in-part of U.S. patent application Ser. No. 12/799,252 entitled "Computing Systems And Methods For Electronically Indicating The Acceptability Of A Product" filed Apr. 20, 2010. The entire disclosures of said applications are incorporated by reference herein for all purposes.

FIELD OF THE INVENTION

The present invention relates to computing systems and methods for electronically indicating the acceptability of a product.

BACKGROUND OF THE INVENTION

Medical and health care products are usually marked with a "shelf life expiration" or "use by" date to enable medical practitioners, healthcare workers, patients and the public to determine whether or not to use a medical or healthcare product. The expiration date is generally marked prominently displayed on the product label. The label may also contain a variety of additional information, including product name, manufacturer name, location and date of manufacture, lot/batch number, and storage conditions. Meats, fish and other food products obtainable at a supermarket are usually marked with a "sell by" or "use by" date to help customers to consume or otherwise use the food products while it is still acceptably fresh. In the case of fresh or frozen meats and fish, the "sell by" or "use by" date is generally marked on a label which is prominently displayed on the product. The label can also contain a variety of additional information, including a product description, price information, weight information, and nutritional information. Other perishable products including various personal care products and industrial products can also bear a "use by" date.

Monitors are devices used to track the exposure of a host product to one or more particular conditions, such as, temperature. Monitors, such as environmental monitors, may be calibrated to indicate the presence of certain environmental conditions, or when certain environmental conditions surpass pre-set limits. Some monitors provide a visual or electronic signal to make such indications.

Use of monitors in product labels can give consumers, patients or other end users some assurance that a given product is acceptable for use by providing some degree of protection against using products that may be ineffective or spoiled because of aging or adverse conditions.

Other factors can also detract from the acceptability of commercial products. For example, a product may be counterfeit and have little or no acceptability. Some measures taken to prevent or identify counterfeit products include various track-and-trace methods which can trace the movement of a product from its manufacturer or other legitimate source to a consumer or other user to assure authenticity. Radio-frequency identification (RFID) and barcodes are two technology methods which can be used to help implement traceability. RFID devices can be incorporated in packages, package labeling, or other product labeling.

Regulatory agencies in the United States and elsewhere have implemented—or are contemplating implementing—"pedigree" requirements for pharmaceutical products. A pedigree is, for example, a certified record that contains information about each distribution of a prescription drug which can be electronically embodied in what is known as an "epedigree".

SUMMARY OF THE INVENTION

In certain embodiments, the present invention may provide a method comprising analyzing by an image capture and communication device a product label for a host product, the product label comprising at least two of one or more environmental monitors, one or more authentication elements, and one or more identification elements, determining by the image capture and communication device a type and one or more features based on the type for each of the at least two of the one or more environmental monitors, one or more authentication elements, and one or more identification elements, accessing by the image capture and communication device a host server, transmitting by the image capture and communication device to the host server data based on the type and features for each of the at least two of the one or more environmental monitors, one or more authentication elements, and one or more identification elements, receiving by the image capture and communication device from the host server an acceptability report based on the data for the at least two of the one or more environmental monitors, one or more authentication elements, and one or more identification elements, and outputting by the image capture and communication device the acceptability report.

In another embodiment, the present invention may provide a method comprising receiving by a host server one or more messages from one or more image capture and communication devices, the one or more messages including one or more acceptability for use data having authenticity, product identity, and current environmental data for one or more host products, determining by the host server whether the host server has access to at least one environmental history for each of the one or more host products, tabulating by the host server one or more second messages including one or more second acceptability for use data for the one or more host products, wherein the one or more second acceptability for use data is tabulated based on the acceptability for use data and, if the host server has access to at least one environmental history for each of the one or more host products, the at least one environmental history foe each of the one or more host products, and transmitting by the host server to the one or more image capture and communication devices the one or more second messages.

In one embodiment, the invention relates to a method that includes (a) analyzing by an image capture and communication device a product label for a host product, the product label comprising at least two of one or more environmental monitors, one or more authentication elements, and one or more identification elements; (b) determining by the image capture and communication device a type and one or more features based on the type for each of the at least two of the one or more environmental monitors, one or more authentication elements, and one or more identification elements; (c) accessing by the image capture and communication device a host server; (d) transmitting by the image capture and communication device to the host server data based on the type and features for each of the at least two of the one or more environmental monitors, one or more authentication elements, and one or more identification elements; (e)

receiving by the image capture and communication device from the host server an acceptability report based on the data for the at least two of the one or more environmental monitors, one or more authentication elements, and one or more identification elements; and (f) outputting by the image capture and communication device the acceptability report.

One or more environmental monitors, one or more authentication elements, and one or more identification elements can include one or more RFID or near field communication (NFC) devices. One or more identification elements can include an RFID device or an NFC device or barcode or other identifier. One or more authentication elements can include the one or more environmental monitors and the one or more identification elements.

The step of (a) analyzing can further include transmitting an interrogation signal to an RFID device. In one embodiment, outputting is graphically displaying, audibly outputting, or graphically displaying and audibly outputting. The image capture and communication device can be a smartphone having a camera. The image capture and communication device can be a computer and a camera. The image capture and communication device can include a barcode scanner. The image capture and communication device is one or more image capture and communication devices. The host server can include one or more processor-based devices such as one or more computers having one or more memory and one or more non-transitory computer readable storage media. In one embodiment, the host server is distributed over more than one physical location. The product label is one or more product labels. The host product can be one or more host products.

In one embodiment, the invention relates to an image capture and communication device. The device can include (a) one or more memories each having at least one region for storing computer executable program code; and (b) a processor for executing the program code stored in the one or more memories, wherein the program code comprises: (b)(i) code to analyze a product label for a host product, the product label comprising at least two of one or more environmental monitors, one or more authentication elements, and one or more identification elements; (b)(ii) code to determine a type and one or more features based on the type for each of the at least two of the one or more environmental monitors, one or more authentication elements, and one or more identification elements; (b)(iii) code to access a host server; (b)(iv) code to transmit to the host server data based on the type and features for each of the at least two of the one or more environmental monitors, one or more authentication elements, and one or more identification elements; (b)(v) code to receive from the host server an acceptability report based on the data for the at least two of the one or more environmental monitors, one or more authentication elements, and one or more identification elements; and (b)(vi) code to output the acceptability report.

In one embodiment, the invention relates to a method comprising: (a) analyzing by an image capture and communication device a product label for a host product, the product label comprising at least two of one or more environmental monitors, one or more authentication elements, and one or more identification elements; (b) determining by the image capture and communication device a type and one or more features based on the type for each of the at least two of the one or more environmental monitors, one or more authentication elements, and one or more identification elements; (c) tabulating by the image capture and communication device data based on the type and features for each of the at least two of the one or more environmental monitors, one or more authentication elements, and one or more identification elements; (e) generating by the image capture and communication device from the host server an acceptability report based on the data for the at least two of the one or more environmental monitors, one or more authentication elements, and one or more identification elements; and (f) outputting by the image capture and communication device the acceptability report.

In one embodiment, the invention relates to a computer-readable non-transitory storage medium having computer executable software code stored thereon, the code comprising: (a) code for analyzing by an image capture and communication device a product label for a host product, the product label comprising at least two of one or more environmental monitors, one or more authentication elements, and one or more identification elements; (b) code for determining by the image capture and communication device a type and one or more features based on the type for each of the at least two of the one or more environmental monitors, one or more authentication elements, and one or more identification elements; (c) code for tabulating by the image capture and communication device data based on the type and features for each of the at least two of the one or more environmental monitors, one or more authentication elements, and one or more identification elements; (e) code for generating by the image capture and communication device from the host server an acceptability report based on the data for the at least two of the one or more environmental monitors, one or more authentication elements, and one or more identification elements; and (f) code for outputting by the image capture and communication device the acceptability report.

In one embodiment the invention relates to a method comprising: (a) analyzing by an image capture and communication device a product label for a host product, the product label comprising at least two of one or more environmental monitors, one or more authentication elements, and one or more identification elements; (b) determining by the image capture and communication device a type and one or more features based on the type for each of the at least two of the one or more environmental monitors, one or more authentication elements, and one or more identification elements; (c) determining by the image capture and communication device whether a host server is available; (d) responsive to determining that the host server is not available: (d)(i) storing in the image capture and communication device data based on the type and features for each of the at least two of the one or more environmental monitors, one or more authentication elements, and one or more identification elements; (d)(ii) determining by the image capture and communication device whether the host server is available; (e) responsive to determining that the host server is available: (e)(i) accessing by the image capture and communication device the host server; (e)(ii) transmitting by the image capture and communication device to the host server the data; (e)(iii) receiving by the image capture and communication device from the host server an acceptability report based on the data for the at least two of the one or more environmental monitors, one or more authentication elements, and one or more identification elements; and (e)(iv) outputting by the image capture and communication device the acceptability report.

In one embodiment, the invention relates to a programmed computer system comprising: (a) at least one memory having at least one region for storing computer executable program code; and (b) at least one processor for executing the program code stored in the memory, wherein the program code, when executed: (b)(i) analyzes a product label for a host product, the product label comprising at least two of one or more environmental monitors, one or more authentication elements, and one or more identification elements; (b)(ii) determines a type and one or more features based on the type for each of the at least two of the one or more environmental monitors, one or more authentication elements, and one or more identification elements; (b)(iii) optionally determines whether a host server is available; (b)(iv) optionally responsive to determining that the host server is not available: (b)(iv)(a) optionally stores data in a non-transitory computer-readable storage medium based on the type and features for each of the at least two of the one or more environmental monitors, one or more authentication elements, and one or more identification elements and/or processes the data using the processor to generate an acceptability report; (b)(iv)(b) optionally determines whether the host server is available (b)(v) optionally responsive to determining that the host server is available: (b)(v)(a) optionally accesses the host server; (b)(v)(b) optionally transmits to the host server the data; (b)(v)(c) optionally receives from the host server an acceptability report based on the data for the at least two of the one or more environmental monitors, one or more authentication elements, and one or more identification elements; and (b)(v)(d) outputs the acceptability report generated using the host server or the processor, as applicable.

In one embodiment, the invention relates to a method comprising: (a) analyzing by an image capture and communication device a product label for a host product, the product label comprising at least two of one or more environmental monitors, one or more authentication elements, and one or more identification elements; (b) determining by the image capture and communication device a type and one or more features based on the type for each of the at least two of the one or more environmental monitors, one or more authentication elements, and one or more identification elements; (c) determining whether the type and one or more features indicates that the product label includes one or more of a color reference zone, a reference color area, or an active color-changing area, the color reference zone having a reference area and an active area; (d) responsive to determining that the type and one or more features indicates that the product label includes one or more of the color reference zone, the reference color area, or the active color-changing area: (d)(i) comparing by the image capture and communication device one or more first pixel or color locations of the reference color area to one or more second pixel or color locations of the active area; (c) accessing by the image capture and communication device a host server; (d) transmitting by the image capture and communication device to the host server data based on the type and features for each of the at least two of the one or more environmental monitors, one or more authentication elements, and one or more identification elements and, if the product label includes the color reference zone, the comparison of the one or more first pixel locations of the reference area or reference color area to the one or more second pixel locations of the active area; (e) receiving by the image capture and communication device from the host server an acceptability report based on the data for the at least two of the one or more environmental monitors, one or more authentication elements, and one or more identification elements; and (f) outputting by the image capture and communication device the acceptability report. In one embodiment, the active area includes an active color-changing area.

In one embodiment, the invention relates to the step of (d)(i) comparing further includes: measuring by the image capture and communication device the one or more first pixel or color locations of the reference area or reference color area and the one or more second pixel or color locations of the active area; determining by the image capture and communication device a first RGB value of the reference area or reference color area based on the one or more first pixel or color locations and a second RGB value of the active area based on the one or more second pixel or color locations; converting by the image capture and communication device the first RGB value to a first color space value and the second RGB value to a second color space value; comparing by the image capture and communication device the first color space value to the second color space value.

In one embodiment, the invention relates to a non-transitory computer-readable storage medium having computer executable software code stored thereon, the code for indicating the acceptability of a host product, the code comprising: (a) code for analyzing by an image capture and communication device a product label for the host product, the product label comprising at least two of one or more environmental monitors, one or more authentication elements, and one or more identification elements; (b) code for determining by the image capture and communication device a type and one or more features based on the type for each of the at least two of the one or more environmental monitors, one or more authentication elements, and one or more identification elements; (c) code for determining whether the type and one or more features indicates that the product label includes a color reference zone, the color reference zone having a reference area or reference color area and an active area; (d) code for responsive to determining that the type and one or more features indicates that the product label includes the color reference zone, comparing by the image capture and communication device one or more first pixel locations of the reference area or reference color area to one or more second pixel locations of the active area; (c) code for accessing by the image capture and communication device a host server; (d) code for transmitting by the image capture and communication device to the host server data based on the type and features for each of the at least two of the one or more environmental monitors, one or more authentication elements, and one or more identification elements and, if the product label includes the color reference zone, the comparison of the one or more first pixel or color locations of the reference area or reference color area to the one or more second pixel or color locations of the active area; (e) code for receiving by the image capture and communication device from the host server an acceptability report based on the data for the at least two of the one or more environmental monitors, one or more authentication elements, and one or more identification elements; and (f) code for outputting by the image capture and communication device the acceptability report.

In one embodiment, the invention relates to a method comprising: (a) receiving by a host server data associated with a host product from an image capture and communication device's reading of a product label of the host product, the data comprising an authentication element data and an environmental history monitor data; (b) storing the data in a non-transitory computer readable storage medium; (c) receiving by the host server a second data associated with the host product from a second image capture and communication device's reading of the label of the host product, the second data comprising an updated authentication element data and an updated environmental history monitor data; (d) storing the second data in the non-transitory computer readable storage medium; (e) determining by the host server whether the host product is acceptable for use based on the authentication element data, environmental history monitor data, updated authentication element data, and updated environmental history monitor data; and (f) transmitting by the host server to the second image capture and communication device a third data indicating whether the host product is acceptable to use.

In one embodiment, the invention relates to a method of re-using a host product from a patient or practitioner that withdrew from a clinical trial, the method comprising: (a) receiving by a host server data associated with the host product from an image capture and communication device's one or more readings of a product label of the host product throughout the host product's distribution in the clinical trial, the data comprising product identification, product authentication, and environmental history monitor information; (b) storing the data in a non-transitory computer readable storage medium; (c) determining by the host server whether the host product is acceptable for use by a clinic or a second patient or practitioner based on the product identification, product authentication, and environmental history information; and (d) transmitting by the host server to the image capture and communication device an acceptability report. In one embodiment, a patient identifier can be input using biometric data, such as a finger print or retinal scan. The biometric data can be collected and processed using an image capture and communication device.

In one embodiment, the invention relates to a method of re-using a host product from an end-user in a supply chain that returned the host product, the method comprising: (a) receiving by a host server data associated with the host product from an image capture and communication device's one or more readings of a product label of the host product throughout the host product's distribution in the supply chain, the data comprising product identification, product authentication, and environmental history monitor information; (b) storing the data in a non-transitory computer readable storage medium; (c) determining by the host server whether the host product is acceptable for use by a second end-user based on the product identification, product authentication, and environmental history information; and (d) transmitting by the host server to the image capture and communication device an acceptability report. The non-transitory computer readable storage medium can be one or more non-transitory computer readable storage media, the host server is one or more host servers, the image capture and communication device is one or more image capture and communication devices, and the product label is one or more product labels. The non-transitory computer readable storage medium is one or more non-transitory computer readable storage media, the host server is one or more can be servers, the image capture and communication device is one or more image capture and communication devices, and the product label is one or more product labels. The non-transitory computer readable storage medium can be one or more non-transitory computer readable storage media, the host server is one or more host servers, the image capture and communication device is one or more image capture and communication devices, and the product label is one or more product labels.

In one embodiment, the invention relates to a method comprising: (a) analyzing by an image capture and communication device a product label for a host product, the product label comprising at least two of one or more environmental monitors, one or more authentication elements, and one or more identification elements; (b) determining by the image capture and communication device a type and one or more features based on the type for each of the at least two of the one or more environmental monitors, one or more authentication elements, and one or more identification elements; (c) optionally determining by the image capture and communication device whether a host server is available; (d) optionally responsive to determining that the host server is not available: (d)(i) optionally storing in the image capture and communication device data based on the type and features for each of the at least two of the one or more environmental monitors, one or more authentication elements, and one or more identification elements; (d)(ii) optionally generating by the image capture and communication device, using the processor, a report indicating whether the host product is acceptable to use based on the data for the at least two of the one or more environmental monitors, one or more authentication elements, and one or more identification elements; (e) optionally responsive to determining that the host server is available: (e)(i) optionally accessing by the image capture and communication device the host server; (e)(ii) optionally transmitting by the image capture and communication device to the host server the data; (e)(iii) optionally receiving by the image capture and communication device from the host server an acceptability report based on the data for the at least two of the one or more environmental monitors, one or more authentication elements, and one or more identification elements; and (e)(iv) outputting by the image capture and communication device the acceptability report generated by the processor or the host server as applicable.

In one embodiment, the invention relates to a programmed computer system comprising: (a) at least one memory having at least one region for storing computer executable program code; and (b) at least one processor for executing the program code stored in the memory, wherein the program code, when executed: (b)(i) analyzes a product label for a host product, the product label comprising at least two of one or more environmental monitors, one or more authentication elements, and one or more identification elements; (b)(ii) determines a type and one or more features based on the type for each of the at least two of the one or more environmental monitors, one or more authentication elements, and one or more identification elements; (b)(iii) optionally determines whether a host server is available; (b)(iv) optionally responsive to determining that the host server is not available: (b)(iv)(a) optionally stores data in a non-transitory computer-readable storage medium based on the type and features for each of the at least two of the one or more environmental monitors, one or more authentication elements, and one or more identification elements; (b)(iv)(b) optionally generates a report, using the processor, indicating whether the host product is acceptable to use based on the data for the at least two of the one or more environmental monitors, one or more authentication elements, and one or more identification elements; (b)(v) optionally responsive to determining that the host server is available: (b)(v)(a) optionally accesses the host server; (b)(v)(b) optionally transmits to the host server the data; (b)(v)(c) optionally receives from the host server an acceptability report based on the data for the at least two of the one or more environmental monitors, one or more authentication elements, and one or more identification elements; and (b)(v)(d) outputs the acceptability report generated using the processor or host server as applicable.

Additional Embodiments of Invention

In one embodiment, the invention relates to a method of optically processing a product label implementable using an image capture and communication device. The method includes capturing image data from a product label using a camera, wherein the product label comprises an environmental monitor having a first shape and a monitor state; capturing image data from a first identifier defined by a patterned region using the camera; processing the image data in response to the first shape to identify a first subset of image data obtained with respect to the first environmental monitor; determining the monitor state from the first subset of image data; and generating an acceptability report based upon the determined monitor state. The method can further include the step of processing the image data in response to the patterned region to identify a second subset of image data obtained with respect to the first identifier; and determining a source of the identifier, wherein the acceptability report further comprises information relating to the determined source. The first identifier can be disposed on or near the product label and wherein the processing, determining, and generating steps are performed using the image capture and communication device, and, optionally, the image capture and communication device is configured for communication with a host server for performance of at least one of the processing, determining, and generating steps.

In one embodiment, the image capture and communication device is a mobile device comprising a display and the camera and the acceptability report is human readable. Further, the method can further include the step of controlling an application programming interface used to control the camera to prevent the captured image data from being pre-processed. The image data can include a plurality of frames of image data and wherein the method further comprises differentiating between the plurality of frames and removing optical defects or selecting a frame or frames for subsequent processing. The method can further include the step of adjusting a dynamic range for the image data using the patterned region as a reference, the patterned region comprising a black and white barcode.

In addition, the method can further include the step of displaying an instruction to a user to capture the image data from multiple angles using the camera. In one embodiment, the product label is configured for use with a product that requires cold storage, but that can be exposed to an ambient room temperature for a predetermined time period such that the monitor state undergoes a change detectable in the image data if the predetermined time period is exceeded. The method can further include the steps of determining a first optical density value correlated with the monitor state and comparing the first optical density value with a plurality of optical densities correlated with residual shelf lives of the product. In one embodiment, the method can further include the step of providing an estimated shelf life for the product in the acceptability report. In addition, the method can further include the step of identifying a plurality of ellipses in the image data to locate the first environmental monitor when the first shape is approximately circular.

In yet another embodiment, the method can further include the step of processing the image data to compensate for curvature of an object to which the product label is disposed upon before determining the monitor state. The method can further include the steps of: capturing image data from a second label using the camera, wherein optionally, the second label comprises a second identifier defined by a patterned region; and populating a records management system with event data associated with an event relating to a product associated with the product label and an entity associated with the second identifier. In one embodiment, the event is selected from the group consisting of: vaccination of the entity with the product; delivery of the product to the entity; performing a procedure on the entity; rejection of the product by the entity; consumption of the product by the entity; acknowledgement of the acceptability report by the entity; the entity performing an experiment using the product; and combinations of two or more of the foregoing events. The method can further include the steps of obtaining supplemental label data from the first identifier or other indicia on the label and processing the image data using the supplemental label data.

In part, one embodiment of the invention relates to an automatic processor-based system for processing a product provided with a product label. The system includes a memory and a processor in communication with the memory, wherein the memory comprises instructions executable by the processor to cause the processor to: automatically store a first set of image data in the memory, wherein the first set of image data comprises a first subset of image data containing environmental monitor information and a second subset containing authentication information, wherein the first set of image data is obtained with respect to the product label; process the first subset of image data such that a monitor state is determined; process the second subset of image data such that an authentication state is determined; and display an acceptability report indicating that the product is acceptable if the monitor state satisfies a predetermined acceptance level and the authentication state is verified as authentic. The memory and processor can be disposed in a host server or a mobile device. The memory device further can include instructions that when executed by the processor cause the processor to: automatically store a second set of image data in the memory, wherein the second set of image data comprises a third subset of image data containing entity information, wherein the second set of image data is obtained with respect to a label associated with the entity; and route the monitor state, the authentication state, and entity information to a database.

In addition, in one embodiment, the entity is selected from the group consisting of a patient; a product transport company; a clinical trial administrator; a hospital; a pharmaceutical company; a supplier; a distributor; a quality control service provider; a manufacturer; and a consumer. The image data can be obtained with a camera and wherein the memory device further includes instructions that when executed by the processor cause the processor to control the camera such that the first subset of image data and the second subset of image data captured using the camera is unprocessed image data when stored in the memory. The memory device can further include instructions that when executed by the processor cause the processor to automatically compensate for noise or glare in the first set of image data. The automatic processor-based system can further include a display in electrical communication with the processor and wherein the memory device further comprises instructions that when executed by the processor cause the processor to inform a user, using the display, to capture the first set of image data from multiple angles. The environmental monitor can experience a detectable change in color when exposed to an environmental stimulus damaging to the product.

In one embodiment, the invention relates to a non-transitory computer readable medium for implementing an environmental monitoring scanning and reporting system comprising: computer executable instructions configured as a plurality of software modules wherein the plurality of software modules comprises one or more of a detection module, an optical compensation module, a report generating module, and an image data processing module that, when the processor executable instructions are executed, cause a processor to capture one or more frames of image data from one or more imaging angles, determine a location of a monitor, process image data and generate an acceptability report.

In one embodiment, differential measurements relative to multiple frames of image data, filters, and other compensation routines are used to reduce glare or substantially glare-proof the image processing of a label to better identify, locate and/or read one or more environmental markers such as a freeze specific markers.

BRIEF DESCRIPTION OF THE DRAWINGS

Features and other embodiments of embodiments of the present invention are explained in the following description taken in conjunction with the accompanying drawings, wherein:

FIGS. 2E and 2F illustrate exemplary acceptability reports according to another embodiment of the present invention;

The drawings are exemplary, not limiting. It is intended for items that are labeled with the same number in multiple figures to refer to the same item throughout the figures.

DETAILED DESCRIPTION

Various embodiments of the present invention will now be described in greater detail with reference to the drawings.

Figure 1:
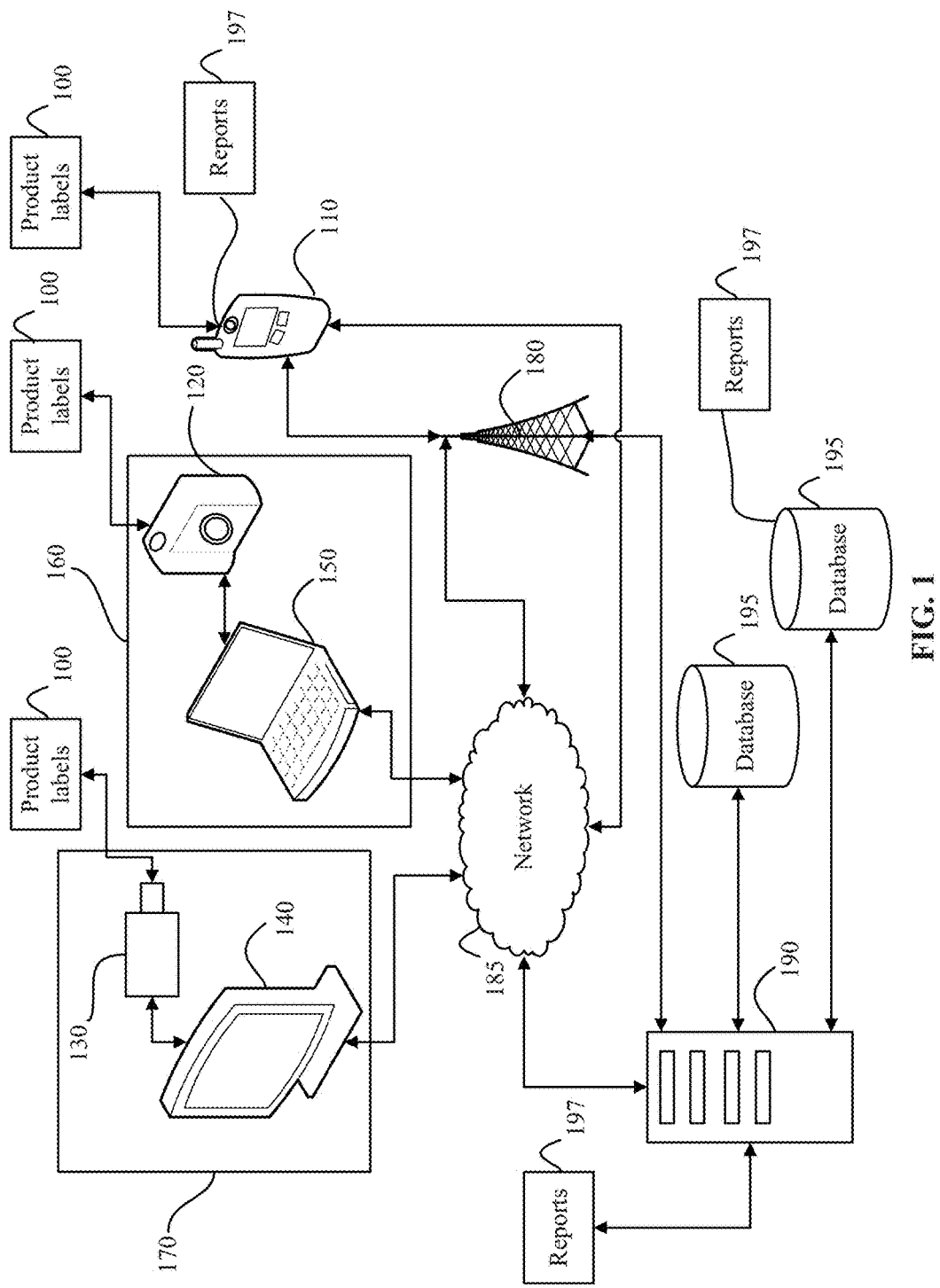
FIG. 1 illustrates a system according to one embodiment of the present invention.

As shown in FIG. 1, one embodiment of the present invention may include one or more image capture and communication devices 120, 130, 140, 150, 170, 160 and 110 directly and indirectly connected to one or more host servers 190 through network 185 or cellular network 180. Host servers 190 may be directly or indirectly connected to one or more databases 195. In one embodiment, a host server can include a server, a server cluster, a mobile device, or any suitable electronic processor-based device or equipment. Image capture and communication devices 170, 160, and 110 may receive data from one or more product labels 100 and optionally store it in such databases 195.

The host server can create or receive various reports 197 such as acceptability reports that can be stored in the databases 195. These reports 197 can be displayed on the image capture and communication devices and indexed or tracked using information on a given label 100. Information captured from an environmental monitor and/or an identifier such as a code disposed on a given label 100 using an image capture and communication device can be used to populate an acceptability report or a database 195 or both.

In one embodiment, the image capture and communication device can include a mobile device that includes a camera or other optical data collection devices. Suitable mobile devices for use with embodiments of the invention can include, without limitation, smart phones, tablets, laptops, and other suitable portable devices. In the following discussion of illustrative embodiments, a "mobile device" includes, without limitation, mobile phones, remote control devices, personal digital assistants, hand-held computers, ultra-mobile personal computers, and the like. The mobile device and methods recited herein may include a mobile internet interface, or web browser. The mobile web browser allows the user to view and otherwise interact with the internet over a wireless network with an internet connection and review reports or access data that relates to a particular label 100. The term "user" refers to an individual using a mobile device. The term "automatically" means without human intervention in one embodiment.

In one embodiment, an image capture and communication device may be any single or set of hardware that is encoded, programmed or otherwise configured to analyze product labels 100 or other labels and transmit data collected from the analysis through a network such as for example network 185 or cellular network 180 to host servers 190 or other predetermined receiving device or system. The image capture and communication device may include one or more non-transitory data storage devices, such as hard drives, RAM, ROM, CD-ROM, DVD-ROM, floppy-disk drives, and/or solid-state memory drives; one or more input devices, such as a keyboard, touchpad, mouse, camera, video camera, image scanner, barcode scanner, densitometer, spectrometer, and/or RFID or a near field communication (NFC) reader; one or more central processing units (CPUs); one or more output devices, such as a display, disc drive, and/or solid-state memory drive; one or more input/output (I/O) communications ports, such as an infrared port, universal serial bus port, serial port, ethernet port, cellular port, HDMI port, Display port, modem port, Bluetooth port, and/or wireless networking controller. The hardware may be in communication with one another by a shared data bus and/or by dedicated connections. The image capture and communication device may have one or more memories with at least one region for storing computer or machine executable program code and one or more CPUs or electronic devices or circuits for executing the program code stored in the memory.

The executable program code may include instructions for reading authentication elements, monitors, and identification elements. The executable program code may include instructions to store data based on the image capture and communication device's review or communication with authentication elements, monitors, and identification elements. The executable program code may include instructions to communicate with a host server, transmit the data to the host server, receive data in response to that transmission, and generate and display a report based on the received data. The executable program code may include instructions to generate a report based on the data obtained from the image capture and communication device's review or communication with the authentication elements, monitors, and identification elements. The executable program code may include instructions to output an interrogation signal to an RFID or NFC device and to receive and/or interpret the data from the RFID or NFC device.

Further, the executable program code may include instructions to read a one-dimensional, two-dimensional, and/or three-dimensional barcode or other glyph, symbol or identifier to receive and/or interpret data from the barcode. The executable program code may include instructions to find and recognize patterns in a particular image. For example, the executable program code may find a section of an image which is similar to a stored template, such as a template of a geometrical pattern, for instance, a solid white or black region or line, a circle, or an ellipse.

In one embodiment, after the desired pattern is located, the pattern can be further analyzed, for example, to interpret the light and dark pixels of a bar code or process a series of ellipses to identify the presence of a monitor having a circular cross section. Such instructions may include routines from a pattern recognition or machine vision software library, for example, Matrox Imaging Library, which contains routines for image analysis and bar code reading. Further, the instructions may include routines configured to identify environmental monitors and compensate for glare or other optical effects that interfere with identifying and otherwise reading an indicator disposed thereon or therein. In one embodiment, the barcodes or identifiers used on the labels can include Data Matrix bar codes and DEGMARKER threshold temperature indicators. Further, the barcodes can include GS1 database fields and the software embodiments described herein are configured to process and extract data therefrom.

In one embodiment, the executable program code includes instructions to store-and-forward data. Such an embodiment may include the image capture and communication device's temporarily storing of data in one or more memories for transmission at a later time, for example, when the host server becomes available, when a network or cellular network becomes available, and/or when transmission price rates decrease.

The executable program code may include instructions for capturing separate values for red, green, and blue (RGB) optical spectral ranges and converting the captured separate values into other color spaces for comparison. For example, grayscale, which is the average of RGB value; or cyan OD, which is the negative of the logarithm to the base 10 of the R value expressed as a fraction of its full-scale value.

In one embodiment, the image capture and communication device 110 is a mobile device with a built-in camera and/or video camera, such as Apple's iPhone® smartphones or iPads, Research in Motion Ltd.'s BLACKBERRY® smartphones or devices that use Google's® Android operating system. For example, Apple's iPhone® 3G or 3Gs or Research in Motion's BLACKBERRY® Bold™ 9700 or Curve™ 8300.

In another embodiment, the image capture and communication device 160 includes a computer 150 connected to a camera 120. In another embodiment, the image capture and communication device 170 includes a computer 140 connected to a camera 130. The cameras 120, 130 can be video cameras or non-video cameras. Computers 140 and 150 can each be a computer that generally includes one or more data storage devices, one or more CPUs, one or more input devices, one or more output devices, one or more I/O communications ports, and other hardware components that facilitate performance of the functions of computers 140 and 150. Computers 140 and 150 may be a tablet PC; alternatively, computers 140 and 150 may be a laptop computer. Cameras 120 and 130 may each be any camera that is directly or indirectly connected to computer 150.

For example, cameras 120 and 130 may be a digital camera connected via USB port or camera 120 and 130 may be a video camera connected to computers 140 and/or 150 by removing a solid-state memory card from cameras 120 and/or 130 and placing it in a solid state memory card reader that is connected to computers 140 and/or 150. Camera 120 and/or 130 may be built into or mounted on computers 140 and/or 150. In another embodiment, an image capture and communication device may include a smart phone tethered to computers 140 and/or 150. Cameras 120 and/or 130 may be connected to a smart phone by removing a solid-state memory card from cameras 120 and/or 130 and placing it in a solid state memory card reader that is connected to the smart phone.

Network 185 may include any type of network infrastructure, such as client/server, peer-to-peer, or hybrid architectures. Network 185 may include the Internet. In one embodiment, cellular network 180 is any cellular network. Cellular network 180 may operate under any mobile telephony standard such as 0G, 1G, 2G, 2G transitional, 3G, 3G transitional, and/or 4G, or another standard. Cellular network 180 may be directly or indirectly connected to network 185 and/or host servers 190.

One or more host servers 190 may be one or more remote computer systems that are accessible over a remote or local network or the Internet, such as network 185, or through wireless network infrastructures, such as cellular network 180. Host servers 190 may have all of the hardware attributes of computers 140 and 150. Host servers 190 may be distributed over two or more physical locations. Host servers 190 may include—or be directly or indirectly connected to—one or more databases 195. One or more databases 195 may be any type of database, such as analytic, operational, hierarchical, network, or relational databases. For example, Microsoft SQL Server, MySQL, Oracle Database, Microsoft Access, Microsoft Excel file, and/or comma separated value or tab-delineated file. In another embodiment, databases 195 may be—or include—any type of data structure, or nested data structures, such as tables, stacks, queues, lists, linked-lists, arrays, trees, and/or heaps. Databases 195 can include medical data such as patient or health care provider data, vaccination data, package shipping, tracking and delivery data, expiration data for one or more products, and other data as described or referenced herein.

Product label 100 may be any product or package label that has one or more monitors, authentication elements, and/or identification elements. Product label 100 may be associated with one or more host products. For example, product label 100 may be placed on—or be part of—the product itself, the product's packaging, or the carton, box, crate, or pallet that houses multiple products for shipping, or be stand-a-lone. For example, in one embodiment, the product label may travel with a truck driver and be associated with one or more host products on the truck.

Examples of host products include perishable health care products, for example vaccines, drugs, medicaments, pharmaceuticals, cosmeceuticals, nutricosmetics, nutraceuticals, and functional foods, medical devices and prophylactics; biological materials for industrial or therapeutic uses, for example cultures, organs and other human or animal body parts, blood and perishable blood products; diagnostic devices, kits and ingredients containing perishables; batteries and battery containing devices and appliances; foodstuffs including fresh or prepared fish, meats, dairy products, fruits, vegetables, baked goods, desserts and the like; food service products, including restaurant service foods; gourmet products; perishable animal foods; cut and uncut flowers; cosmetics, for example cosmetics containing biologics or other labile ingredients; beauty aids; perishable munitions and ordnance; perishable decontamination packs and products; and liquors, for example, wine, beer, champagne, port, whisky, cognac.

Figure 2A:
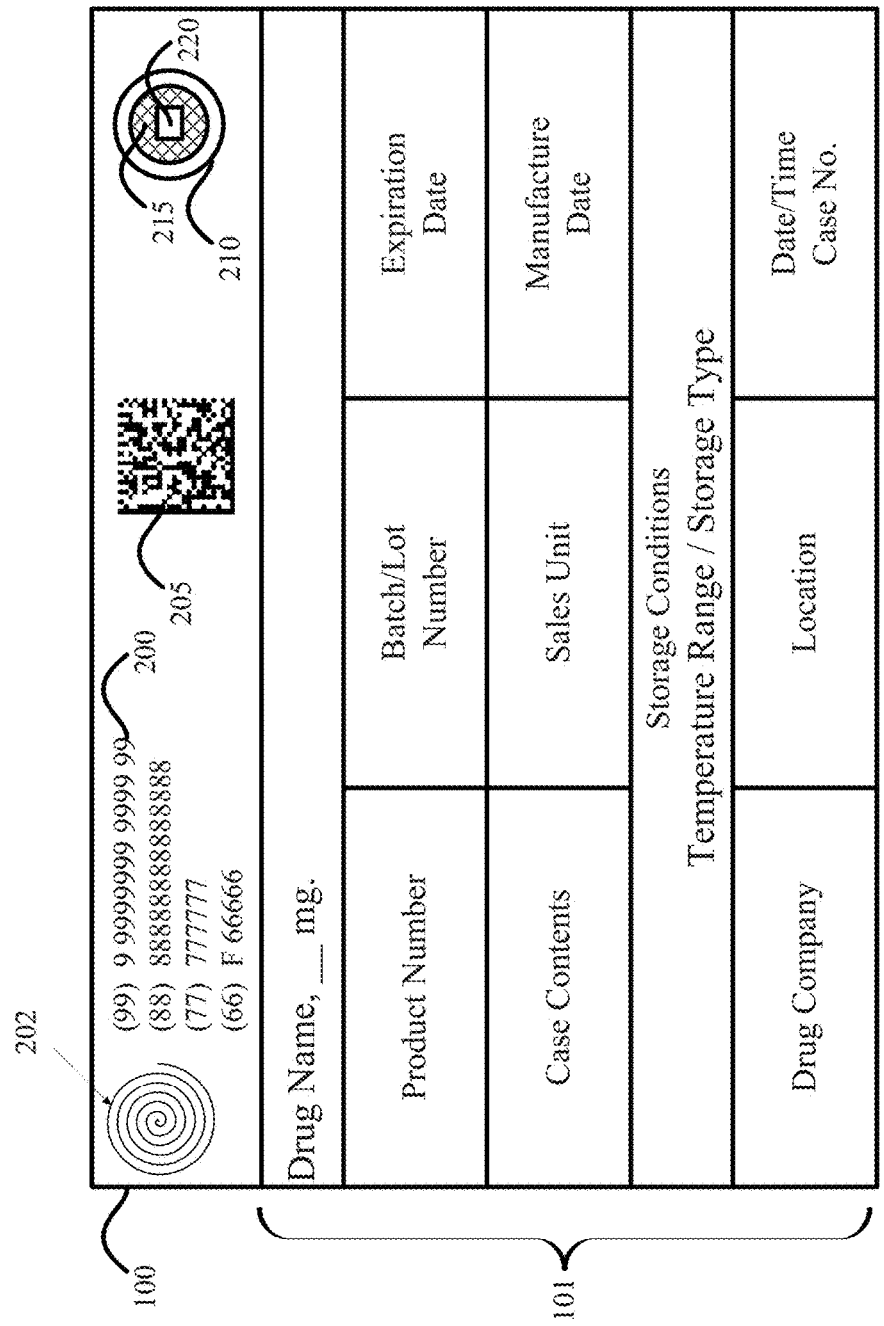
FIG. 2A illustrates a product label according to one embodiment of the present invention.
Figure 2B:
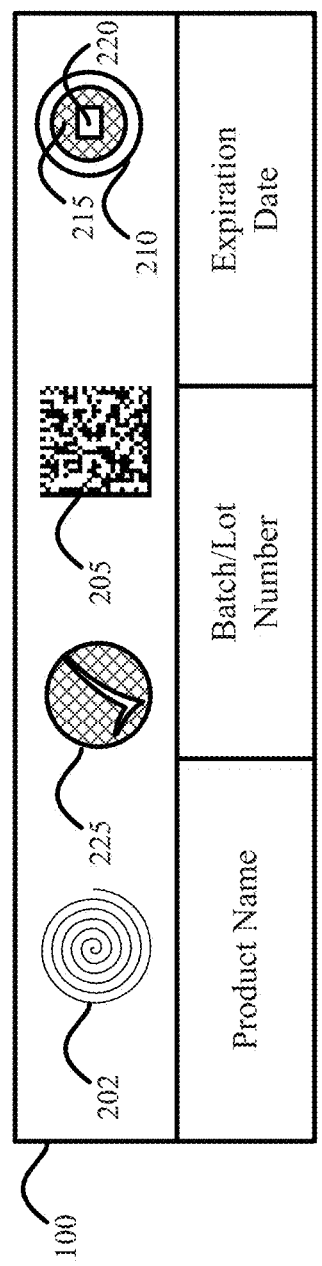
FIG. 2B illustrates a product label according to another embodiment of the present invention.

As shown in FIGS. 2A and 2B according to one embodiment of the present invention, product label 100 may include one or more of monitors 210 and 225, authentication element 202, and/or identification elements 200 and 205 also referred to as identifiers. The label in FIG. 2A includes additional details as indicated in the region of the label 101 below the monitors 210, 225 and authentication element 202. In one embodiment, the information shown in region 101, a subset thereof, additional information or different information can be displayed as an acceptability report as described herein. The monitors may be environmental history monitors. An environmental history monitor may indicate one or more conditions of the environmental history of the host product with which it is associated, for example, the environmental history monitor may indicate past exposure of the host product to one or more environmental conditions. The environmental history monitor's appearance may change with time to indicate the changing value of a monitored condition.

One example of an environmental condition which can be monitored by the environmental history monitor is heat exposure. The environmental history monitor can monitor heat exposure, either as an average cumulative temperature or as the occurrence of a temperature either above or below a specific temperature for a particular duration. Examples of such heat monitoring environmental history monitors may include cumulative time-temperature indicators, freeze indicators, thaw indicators and threshold indicators which can indicate a single event of past exposure to a temperature above ambient, or above another predetermined temperature.

Other environmental conditions which environmental history monitors may monitor include humidity, mechanical shock, gas exposure, oxygen exposure, toxin exposure, chemical exposure, biological agent exposure, actinic radiation exposure, x-ray exposure, and/or microwave exposure.

Various environmental monitors, and various constructions of time-temperature indicators, that display a capturable indicator image, or other capturable indication of a monitor state, can be employed in the practice of the invention will now be described. A monitor, can include a time-temperature indicator ("TTI" herein) comprising one or more colorless, or light-colored diacetylene monomers that develop color as they polymerize. The progressive color development can occur at a rate that increases with temperature. Some examples of suitable time-temperature indicators employing various diacetylenic compounds are disclosed in for example, U.S. Pat. Nos. 3,999,946; 4,189,399; 4,384,980; 5,045,283; 5,053,339, and 5,254,473; to Patel, and U.S. Pat. Nos. 4,789,637 and 4,788,151 to Preziosi et al., U.S. Patent Application Publication Nos. 2008/0004372 by Prusik et al., 2009/0131718 by Baughman et al. and 2011/0086995 by Castillo Martinez et al., the disclosures of each of which patents and patent publications are incorporated by reference herein.

A monitor can include a multifunctional time-temperature indicator which integrates two indicator types into a single device. For instance, such a multifunctional time-temperature indicator can include a primary indicator, which can develop a color change as a result of a particular cumulative time-temperature exposure, and a secondary indicator, which can be set to trigger at a predetermined temperature. Some examples of such multifunctional time-temperature indicators are disclosed in U.S. Pat. No. 5,057,434 to Prusik et al. and U.S. Pat. No. 7,490,575 to Taylor et al., the disclosures of which are incorporated by reference herein.

A monitor can include an activatable time-temperature indicator system that includes a color-forming time-temperature indicator system that may be affixed to a product label so that the indicator composition is coextensive with a barcode. Upon expiration of the useful shelf life of a host product, the color density may reach a level which obscures the barcode sufficiently to register in a barcode reading system, for example, a retail market computer system, as a failed or unsafe product. Some examples of such activatable time-temperature indicators are disclosed in U.S. Pat. No. 6,544,925 to Prusik et al., the disclosure of which is incorporated by reference herein.

A monitor can include a temperature-activatable time-temperature indicator that includes an optically readable, thermally sensitive indicator element that is intrinsically thermally responsive at or above an activation temperature and employs an indicator element that includes a synthetic polymeric material such as a side-chain crystallizable polymer, for example, as disclosed in patent application Ser. No. 13/238,686 by Huffman et al., the disclosure of which is incorporated by reference herein.

A monitor can include a combination radio frequency identification device ("RFID" herein) and environmental condition indicator tag. Information supplied by the RFID, for example, product ID and related data, may be machine read by interrogation of the RFID at an inspection station and the visual condition indication may be optically read by machine at the same station. The signals can be utilized locally at the inspection station or may be used at locations remote therefrom. Some examples of such a combination RFID and environmental condition indicator tag are disclosed in U.S. Pat. No. 7,209,042 to Martin et al., the disclosure of which is incorporated by reference herein. Alternatively, the environmental condition indicator may have electrical properties that may be read by the RFID device. For example, such an indicator could be an environmental indicator based on the etching of an aluminum film by an acid, such as is described in U.S. Patent Application Publication No. 2009/0301382 by Patel et al.

The solid-state polymerization of diacetylene monomers and co-precipitated monomers to polymers are useful as, and in, time-temperature indicators. The monomers can be prepared as active agents on a substrate, or could be activated on demand by a number of methods including solvent evaporation, melt recrystalization, acid formation, metal formation, salt formation or the associated removal of the acid, metal or salt. Some examples of such methods and devices are disclosed in the patent publications referenced previously herein as disclosing time-temperature indicators employing various diacetylenic compounds.

Time-temperature indicators can include an immobilized enzyme which can react with the substrate to produce a color change in time and temperature dependent manner. Photo induced coloration by radiation of spiropyrans having a temperature dependent decoloration can be used as a time-temperature indicator.

Time-temperature indicators can include an upper layer carrying a first reactant and a base layer carrying a second reactant adapted to react with the first reactant upon triggering. TTIs can be formed from thermal paper and an activating film placed on the thermal paper. An indicator can be mixed with a portion of a food product and detects food spoilage directly, for example, pH change, through, for instance, detecting m-nitrophenol, p-nitrophenol and litmus changes from green to red/pink.

A time-temperature indicator may have two surfaces that remain adhered when brought together: an acid-base indicator in one and an activator in the other. A time-temperature indicator can be based on an azo coupling reaction between a capped diazonium component and a coupling component. An enzyme based time-temperature indicator including urease to consume urea to generate ammonia and carbon dioxide, which may cause a pH change causing color change in a pH indicator.

Time-temperature indicators can be prepared from a free radical-sensitive dye and peroxide on a carrier. Time-temperature indicators can include a diffusion layer capable of transition above a defined temperature. An indicator film can be placed on one side of diffusion layer and be separated from a reactant material capable of producing a color change when in contact with the indicator film.

Time-temperature indicators can be produced using vapor permeation techniques. Activatable time-temperature indicator can include an oxygen-sensitive dye coating and a removable oxygen barrier over the coating. In one embodiment, the environmental marker can include a threshold temperature indicator with a delayed color change. In one embodiment, a DEGMARKER is an environmental marker that is configured as a threshold temperature indicator to indicate a temperature excursion above a threshold (e.g. above 40° C.). In addition, a vaccine vial monitor is a time-temperature indicator that is shaped and otherwise configured for use with vaccine vials. Some of the environmental monitors described herein have a reflective coating or cap such as a bubble, laminate layer, substantially hemispherical cap, or other surface which can cause glare or other unwanted optical effects. A human viewer can overcome such adverse optical effects using various perceptual skills. However, when a machine or camera is used to capture image data with respect to a color sensitive indicator, glare or other optical effects can lead to incorrect results or cause the processing system to fail.

In part, such problems can occur because detection algorithms used to identify a circular environmental monitor or other regularly shaped monitor may attempt to find a master shape which encompasses the regular shape as it appears when viewed from different perspectives. For example, in the case of a circular monitor, the image data collection system is configured to implement an ellipse tracking routine because from a non-top down viewing angle, the circle is seen as an ellipse. Various processor-based methods for addressing this are described below. Notwithstanding the foregoing, in some embodiments, the environmental monitors can include a matte finish or an anti-glare layer to improve monitor detection during optical processing. In addition, given a set of known issues, such as expected color changes or colors that are difficult to resolve, or color ranges associated with various monitor configurations, the software modules configured to process image data can be sensitized to certain colors or otherwise pre-configured based on monitor-specific characteristics. For example, some cameras may have difficulty detecting a red state associated with an expired condition. Accordingly, the software module can specify a low red threshold or window to improve the likelihood that such a monitor state will be detected when it exists.

In one embodiment, the authentication element 202 may establish or verify the authenticity of the host product with which the monitor is associated. The authentication element may be readable by a human or a machine. For example, the authentication element can include an area printed with a special ink, a symbol, or an object which is difficult to reproduce and which, in other embodiments, may also visually change with time. The authentication element may be incorporated into the identification element and/or monitor. The identification element may include information referencing the authentication element. If such information, for example, fails to verify the authentication element 202, a person or a computer scanning or reading the element can determine that the label and possible the product to which it is applied is counterfeit.

In one embodiment, the authentication element 202 can provide capturable information enabling the host server, or another suitable remote entity, to verify, or evaluate the authenticity of the host product. Some embodiments of the invention can enable the host server, or another suitable remote entity, to interpret information from the authentication element to determine that the host product is authentic, or is counterfeit and does not originate from a supplier of the authentic host product, or is diverted, or parallel traded, and originates from the supplier of the authentic host product, but has been distributed through an unauthorized distribution channel. Some or all of this information can be included in an acceptability report, if desired. The host server, or another suitable remote entity, can use information captured from the authentication element and the identification element, if employed, to help determine authenticity, for example, by consulting a database to determine whether a combination of information captured from the authentication element and the identification element is a valid combination of information indicating an authentic host product. Information captured from the environmental monitor can also be employed to help evaluate the authenticity of the host product, if desired.

In one embodiment, the identification element indicates the identity of the host product. For example, an identification element may include a one-dimensional barcode, a two-dimensional barcode, a three dimensional barcode, or an RFID device. The identification element can be printed and be visible to a human and/or machine-readable. For example, the identification element can be printed with an ink that reflects primarily in the near-infrared and can be read with a digital camera that is sensitive to near infrared light. The identification element can be accompanied by a human readable equivalent of the identification element, for example a string of text, icons, pictographs or other human-recognizable graphics or symbols.

By way of further example, an authentication element or identification element employed in the practice of the invention can include an optically readable graphic, symbol, indicia, mark, character, alphanumeric character, or pattern, or a combination of any individual one, or multiple ones, of the foregoing optically readable elements. The optically readable element, or elements, can be rendered in any suitable medium, or media, for example, an optically variable diffractive device, or other device, that creates a change in appearance when viewed from different angles, a color-shifting ink, a hologram, a microlens array, iridescence, luminescence, a guilloche, a thermochromic ink, infrared ink, machine-readable optical information, microtext, nanotext, microscopic graphics, pen revealable marking, laser authentication, watermarking, digital watermarking, metamerism, embossing, intaglio printing, or a combination of two or more of the foregoing media. The authentication element can be overt, which is to say, apparent and visible to the human eye, unaided by special viewing equipment such as a microscope not normally employed by the viewer for reading, or covert, which is to say having a concealed or hidden feature, or features, that is, or are, not apparent, and can only be viewed with special reading, or viewing, equipment.

The identification element may be unique and identifies the host product with which it is associated. The identification element may include an item identifier that indicates the identity of a specific individual host product for example a stock-keeping unit.

In one embodiment, the identification element may include a serial global trade identifier number (SGTIN). For example, a "SGTIN-96" tag. A SGTIN-96 tag data specification provides six fields that are to be set for each tag and the combination of all six fields ensures each tag's uniqueness. The six fields are as follows: a header comprising 8 bits; a filter, comprising three bits which can specify if the tagged object is an item, case or pallet; a partition, which is three bits and indicates how the subsequent fields are divided to get the correct data for each; a company prefix, which comprises 20-40 bits (depending on the partition); an item reference, comprising 24-4 bits (depending on the partition) which can comprise the item's global trade identification number "GTIN"; and a serial number, which is 38 bits and contains the item's unique serial number.

The identification element may be compatible with an e-pedigree code used for pharmaceutical tracking. In one embodiment where the identification element includes an RFID or other electronic device, the identification element may include an electrical or optical device to read the other elements of product label 100, such as one or more monitors 210 and 225 and/or authentication element 202. Monitors, such as environmental history monitors, may generate both electrical and visual signals indicating exposure to one or more environmental conditions. Such electrical signals may be output to an associated RFID that otherwise acts as an identification element.

The information from monitors 210 and 225, authentication element 202, and identification elements 200 and 205 of product label 100 may be accessible by photocapture, scanning, pattern recognition, image comparison, such as by using image capture and communication devices 110, 160 and 170, or by human recognition.

As shown in FIG. 2A according to one embodiment of the present invention, product label 100 may be configured for attachment to a case containing one or more sales units of a pharmaceutical product. Product label 100 may be self-adhesive or otherwise attachable to the case. Product label 100 may be printable in a single pass or in multiple passes. The entire label 100 may be printable. One or more monitors, authentication elements, and/or identification elements may be separately fabricated and then attached or applied to label 100. It is noted that product label 100 may include one or more monitors, authentication elements, and/or identification element that are not physically embedded or otherwise located on the same surface or housing; however, in such an embodiment, the monitors, authentication elements, and/or identification elements would be associated with the same one or more host products.

As shown in FIG. 2A according to one embodiment of the present invention, label 100 may include in a header row at the top of the label, identification element 200, a two-dimensional barcode 205, and monitor 210. Beneath the header row, the label has the drug name and strength, prominently displayed. Beneath the drug name appear additional data, such as, a product or list number, for example, 1 55Z5555 555 555; a batch or a lot number, for example, F 66666; an expiry date for the drug or other host product; a notation as to the case contents, for example, 10 units per case; a sales unit description, for example, 2 syringes per carton; a date of manufacture of the drug; storage conditions such as a permissible range of temperature variation and a storage type, for example, refrigerated storage; the name of the supplier; the location of the manufacturing plant; and the date and time of dispatch and a case number, for example, 72/1000. Identification element 200 may include a product number which may be the same as or different from the product/list number. The identification element 200 may be the same as or different from the product expiration date and a batch or lot number. Some or all of the information in identification element 200 may be encoded into identification element 205. Identification element 205 can include one or more authentication elements, for example, a serial number or a code correlated with other information on label 100, which uniquely identifies the host product unit, for example, a case, and hinders counterfeiting. Authentication element 230 may include one or more identification elements. In another aspect, monitors 210 and/or 225 may include one or more identification and/or authentication elements.

In one aspect, monitor 210 is an environmental history monitor that operates as a time-temperature indicator. The monitor 210 can be read once a subset of image data associated with it is determined to provide a monitor state such as whether the monitor was or was not exposed to an unacceptable temperature range. In addition, the identification element 200 can be an identifier, such as a barcode or other symbol or code that contains information therein or contains links to a database to identify a file and related information associated with an entity, person, or object. In one embodiment, the identifier can include a patient identifier, a biological specimen identifier, such as an identifier of an organ for transplant or of other biologic material, package shipping, tracking, rejection, delivery or other similar information, a clinical trial participant related identifier or a candidate drug identifier, or other source of information suitable for encoding or using the identifier or accessing a database using the identifier. A patient identifier can include biometric information, such as a finger print, a retinal image, or other patient specific biological features suitable for imaging using a mobile or fixed camera or imaging system.

In one embodiment, monitor 210 is an environmental history monitor that operates as a time-temperature indicator. Monitor 210 can include two or more color regions, such as, an active zone 220 and an optional reference zone 215, which zones can have any suitable shape. For example, active zone 220 can be rectangular, as shown, square, polygonal, circular, strip-like, or have another regular shape or an irregular shape, and reference zone 215, if employed, can have a circular outer periphery and extend around, or surround, active zone 220, as shown, or can have another shape and/or disposition.

Active zone 220 can change color. For example, active zone 220 can darken in response to cumulative temperature exposure over time that is outside of acceptable limits for the host product. This color change can be a monitor state. If active zone 220 appears as dark as or darker than reference zone 215, monitor 210 is indicating, by visual signal, that the host product with which it is associated is no longer acceptable for use, or may no longer be acceptable for use. The degree of darkening can relate quantitatively to the cumulative time-temperature exposure experienced by monitor 210. An appearance of active zone 220 that is less dark than reference zone 220 can indicate that an associated host product may have an acceptable condition.

In another embodiment, active zone 220 can lighten in response to cumulative temperature exposure over time that is outside of acceptable limits for the host product. In such an embodiment, if active zone 220 appears lighter than reference zone 215, monitor 220 is indicating, by visual signal, that the host product with which it is associated is no longer acceptable for use, or may no longer be acceptable for use.

In a further embodiment, any suitable color parameter, or combination of color parameters, detectable in active zone 220 can be compared with the corresponding color parameter or color parameters detectable in reference zone 215, for example, grayscale reflectivity, grayscale density, color optical density, RGB values, Lab values, brightness, hue and/or color intensity. Any of these comparisons can indicate a monitor state. In a further embodiment of the invention, reference zone 215, can include multiple sections for example from two to six sections, with different appearances corresponding with different cumulative time-temperature exposures, which can indicate different conditions the host product may have, for example, "fresh", "still fresh", "use now", and "not acceptable".

An acceptability report can include a corresponding indication of the probable condition of the host product derived from information imaged from active zone 220 and, optionally, from reference zone 215. These zones can be stored in memory of a device such as a mobile device and processed as subsets of a set of image data. Any of the color parameters or other optical parameters associated with an environmental monitor disposed on a product label can be analyzed with respect to reflectance parameters, dynamic range, ambient light levels and other parameters using image data captured on a per frame basis by a camera.

Further, an identifier, such as a barcode, graphic symbols, indicia, or other marks can be used as supplemental label data to help process the image data with greater accuracy or speed. Supplemental label data can inform the software performing the image data processing about the shape of an object upon which the label is disposed, about the type and characteristics of the environmental monitor on the label, about the relative spatial positions of elements on the label, about tracking information relating to when the identifier was previously scanned, and/or about any other parameter relating to the elements on the label.

With respect FIGS. 2A and 2B, a given label 100 can include a substrate which may be paper, plastic or another material. The substrate may be part of a box, vessel, parcel, package, or other container, and label 100 can be disposed thereon. The container can contain one or more host products or host product items. The elements 202, 225, 205, 210, 215, and 220, variously, can be disposed on or in the substrate and positioned adjacent to each other, or at predetermined distances from one another, such that a given element serves as a fiducial relative to another element or elements, or to a border or a boundary of the label. A given label can include a border, a boundary shape or shapes or other geometric elements that can be resolved relative to a given background and elements disposed on the label while image data is being captured by the camera. Such geometric elements or borders can be used by a detection or a processing module to identify which element is a barcode, text, a monitor or another element. These geometric elements can also be configured to serve as authentication elements. Once identified, each element on the data can be read from the relevant pixels or subset of image data associated with each respective element.

Figure 2C:
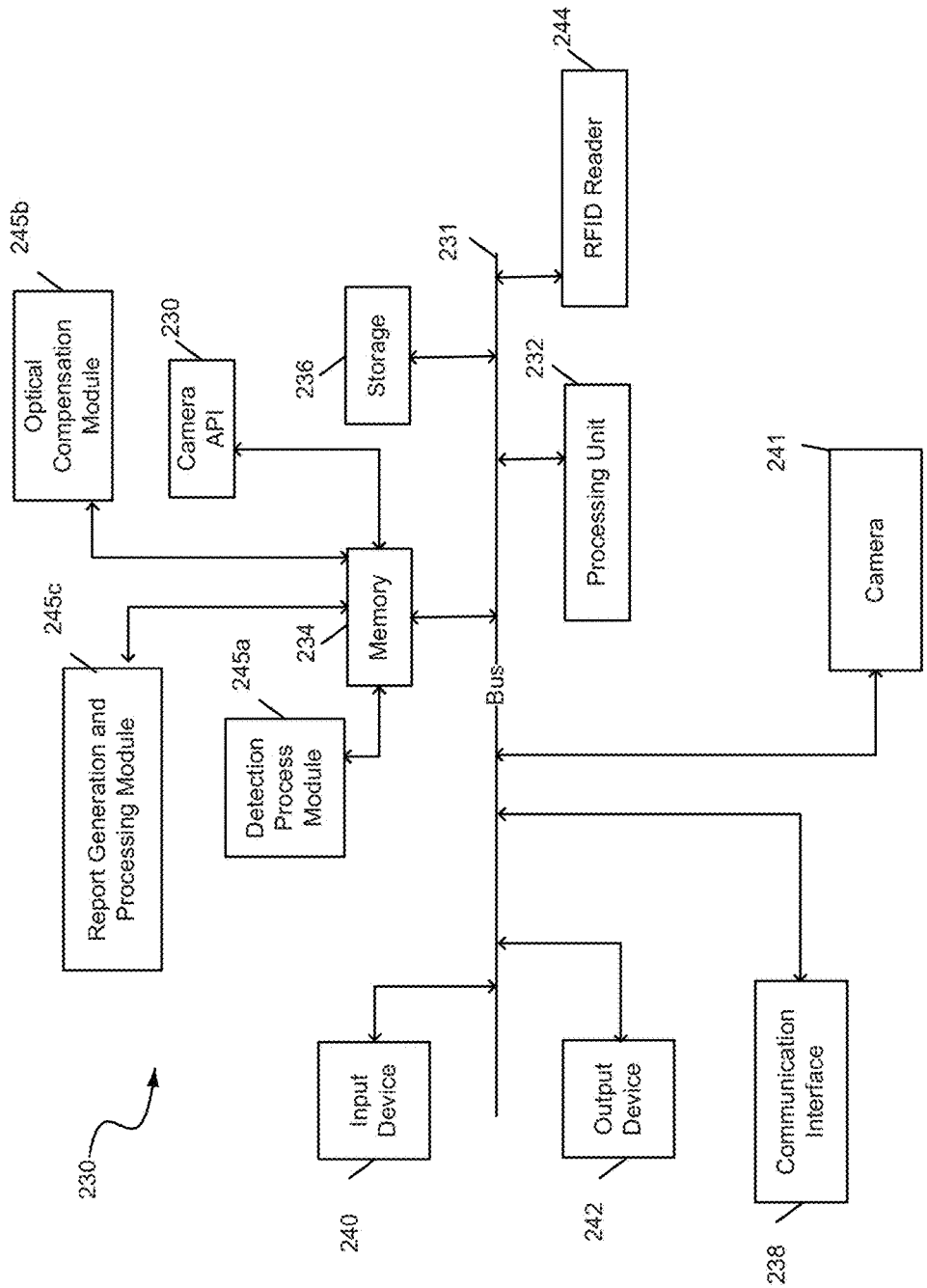
FIG. 2C illustrates a mobile device and related components and software modules according to another embodiment of the present invention.

FIG. 2C is a functional block diagram that illustrates the components of an exemplary mobile device 230 for practicing an embodiment of the present invention. Mobile device 230 preferably includes a system bus 231, processing unit 232, a system memory 234, storage 236, a communication interface 238, an input device 240, a camera 241, an output device 242 and a RFID reader 244. System bus 231 couples system components including, but not limited to, system memory 234 to processing unit 232. The processing unit 232 can be any of various available processors. In one embodiment, the processing unit 232 can include a central processor, a graphic processor, other processors or combinations thereof. Various software modules or applications can be executed by the processing unit 232 and stored in memory 234 or storage 236. As shown, a detection process module 245a, an optical compensation module 245b, and a report generating and processing module 245c, as well as various other modules can be used.

Input device 240 may include, but is not limited to a keyboard, touchscreen or any generalized touchscreen that responds to a user initiated contact, which can be used to receive data from a user. In addition, input device 240 can also include a plurality of other inputs or controls for adjusting and configuring one or more embodiments of the present invention including voice commands. Output device 242 may be a display device, such as an LCD or LED display screen, that can display one or more configurable icons, buttons, input boxes, menus, tabs, and so forth to facilitate user control of the mobile device 230, 230'. A touch screen or other input or output devices can be configured to initiate and respond to instructions relating to imaging a label 100 and capturing information with respect to the labels constituents using the device's camera. Reports and other data such as image data can also be displayed using output device 242. The captured image data can be used to determine if the product label is authentic, confirm source information, or process an environmental monitor to determine if a monitored host product is still good or provide other information about the host product, for example, that the host product has been exposed to excessive heat or cold and information about a likely residual useful life of the host product. Expiration dates can also be recalculated or changed, based on captured image data for a given label, and can be included in the acceptability report, referred to a host server, and/or utilized in another manner.

In one embodiment, communication interface 238 facilitates data exchange through an interface to and from various platforms and systems such as a hospital, medical record repository, shipping company, storage area networks, host servers, drug suppliers, biologic suppliers, governmental entities and other suitable entities such as for example entities that provide an identifier suitable for use with a label 100. Thus, this interface can be used to send and receive reports 197 and initiate queries with respect to the databases 195 such as to access records associated with an environmental monitor or identifier. The hardware and software useful for connection to the communication interface 238 includes, for exemplary purposes only, internal and external components that transmit and receive data wirelessly across a plurality of standard protocols including, for example, PCS, GSM, CDMA, Bluetooth, Wi-Fi, IrDA, WiMAX, or through other known wireless standards.

Storage 236 or memory 234 may include removable or fixed, volatile or non-volatile or permanent or re-writable computer readable storage media. The computer readable medium can be any available medium that can be accessed by a general purpose or special purpose mobile device. By way of example, and not limitation, such a computer readable medium can comprise flash memory, RAM, ROM, electrically erasable programmable read only memory (EEPROM), optical disk storage, magnetic disk storage or other magnetic storage devices, or any other medium that can be used to store digital information on a mobile device.

It is to be appreciated that FIG. 2C illustrates software that can act as an intermediary between a user and the basic resources described in mobile device 230. Such software preferably includes an operating system and one or more software modules configured to process labels 100 and other features of the invention. The operating system, which can be resident in storage 236, can act to control and allocate resources of mobile device 230. System applications take advantage of the management of resources by the operating system through program modules and program data, image data, and/or monitor data stored either in system memory 234 or on storage 236. Furthermore, it is to be appreciated that the present invention can be implemented with various operating systems or combinations of operating systems. Additional details relating to the software architectures and software modules suitable for use in an embodiment of the invention are shown in FIG. 2D.

The computer readable medium tangibly embodies a program, functions, and/or instructions that cause the mobile device or other suitable image capture and communication device to operate in a specific and predefined manner as described herein. Those skilled in the art will readily appreciate, however, that the process described below may be implemented at any level, ranging from hardware to application software and in any appropriate physical location. For example, the present invention may be implemented as software code to be executed by mobile device 230 using any suitable computer language and may be stored on any of the storage media described above, or can be configured into the logic of mobile device 230. Such software code may be executed by mobile device 230 using any suitable programming language, such as C, and using a graphic processing unit and a central processing unit in parallel.

Prior to discussing some of the software components in more detail it is informative to consider the general operation of a mobile device relative to an exemplary interaction with a label 100 such as shown in FIGS. 1, 2A and 2B. FIG. 2D shows an exemplary mobile device 230' that can include all or a subset of the components shown in FIG. 2C or additional features or embodiments relating to the present invention as described herein.

Figure 2D:
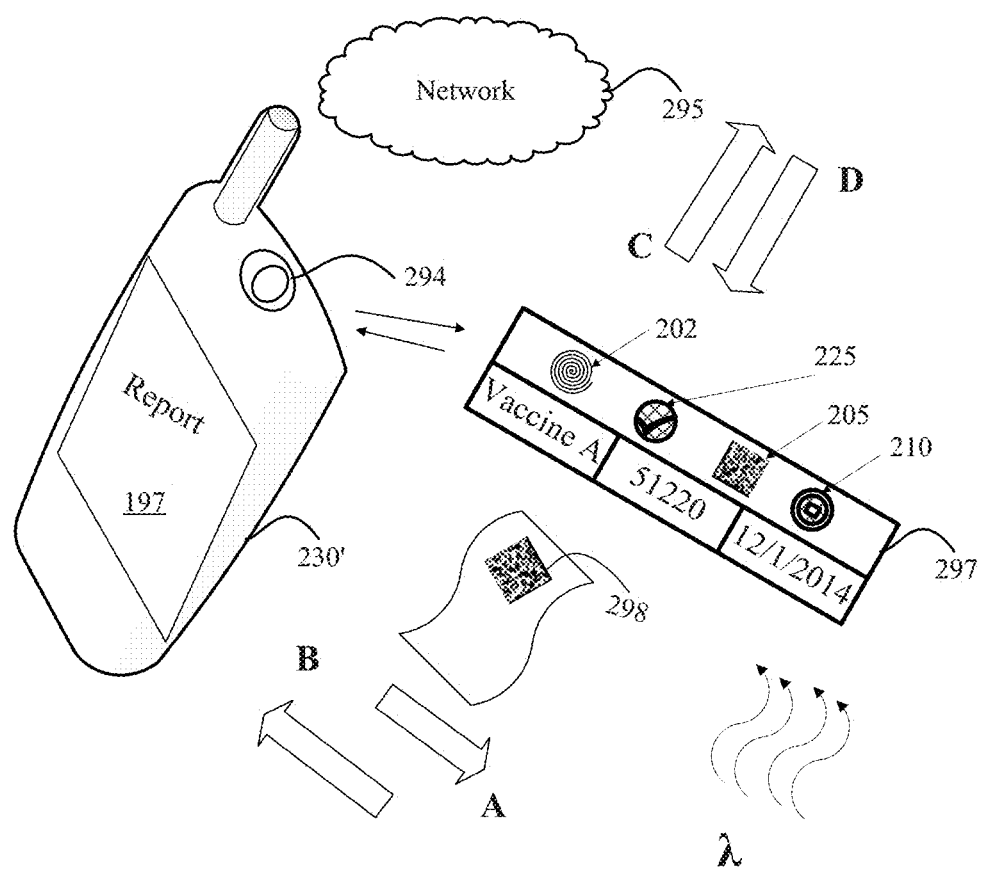
FIG. 2D illustrates a mobile device configured to capture image data from a product label according to another embodiment of the present invention.

More specifically, FIG. 2D shows a mobile device 230' having a flash-equipped camera 294 in communication with a network 295 and disposed in juxtaposition to a product label 297 to image the product label 297. A non-product label or another product label 298 is also shown. For the purposes of explanation the product label 297 includes the information shown in label 100 in FIG. 2B. The camera can be a video camera or a non-video camera such as a still camera. The camera is configured to capture one or more image frames imaging a part of product label 297, or the entire label. In one embodiment, a user can inspect label 297 and manually hold the camera in the juxtaposition shown to capture information on the label including information relating to the authentication, the identifier, and a monitor, as shown in FIG. 2D.

Although the label 297 is shown as one continuous label, in one embodiment, one or more labels or imageable elements can be provided, optionally from different sources. Thus, a second label or other object 298 can also be imaged before or after label 297 is imaged as a first label. The second label or other object 298 can include identifiers, monitors and other elements as described herein relative to label 100, 297 and otherwise. In one embodiment, the second label or other object 298 can include an identifier such as a barcode or other scannable or imageable element associated with a patient, such as a hospital bracelet with a barcode, a tracking or shipping company label, an organ transplant tracking device, or other type of label or tracker that relates to the use, storage, consumption, transport of the product having label 297.

In response to capturing one or more frames of image data of the label 297 from one or more positions, a report 197 such as an acceptability report can be displayed on the mobile device 230 using its display or touch screen as applicable. For example, report 197 can be an acceptability report on the acceptability of a host product associated with label 297 and/or second label or object 298. Report 197 can be in human-comprehensible format for example in text or other written characters, optionally accompanied by graphics, icons or the like. Usefully, report 197 can be comprehended, or read, without undue difficulty, by an average literate adult, without using special equipment. If desired, report 197 can be output from mobile device 230' to a printer, for example via an IR interface, and printed on paper, or an equivalent. Further, report 197 can be output audibly, if desired, for example, from an audibilizing component of mobile device 230'. In one embodiment, to simplify the user experience, when data is being captured, data capture can occur over time and, optionally, multiple frames can be captured from one or more viewing angles relative to the label 297. In one embodiment, the best frames are used and others are dropped. While in another embodiment, frames of image data can be compared to one another and the results used to compensate for glare and to identify the different elements present in or on a given label.

In one embodiment, the process starts with a user selecting an application on the device 230' relating to scanning a label or evaluating a product identifier or another process. In response to that selection, a graphic user interface can present the user with various options and instructions. In some cases, the instructions can address lighting considerations, optionally based upon information obtained by device 230' from detection of ambient lighting conditions. The instructions may indicate that the ambient lighting conditions are such that the label cannot be imaged and can initiate one or more light pulses from the flash during image data collection. Alternatively, device 230' can instruct the user to use an external light source such as a lamp or sunlight. Since color perception depends on the color balance of the incident light, it may be advantageous in some cases to employ light of known color balance using a lighting source which may be available for taking pictures with the image capture and communications device. In one embodiment, the flash can be controlled to supply light having a predetermined color balance.

Alternatively, by using a standard light source, external to the imaging device, enhanced measurement of color levels may be obtained. A user interface can display instructions to a user relating to whether or not external light is needed. However, in some embodiments of the invention, the mobile device and camera can collect desired label data without employing external lighting, simplifying the data collection process for a user. Data collection can be handled using multiple frames of data as outlined below in one embodiment.

As shown in FIG. 2D, mobile device 230' is positioned relative to a label 297 having various elements disposed therein as described herein with respect to FIGS. 2A, 2B, and elsewhere. Image data can be collected using the camera 294 in the presence of light λ which can be ambient light, one or more flashes from mobile device 230', an external light source or other types of light. In one embodiment, one frame of image data captured using the camera 294 with respect to the label 297, and/or label 298, may be sufficient to perform one or more of: authenticating of element 202, identifying monitors 210 and 225, obtaining a reading or exposure level from monitors 210 and 225, identifying and processing an identification element 205, such as a 2D barcode, and capturing any other text or information such as the product information shown in FIG. 2D, namely, product name "Vaccine A," reference number "51220" and the date "12/1/2014." Once these processes are performed or the data is collected, the image data can be relayed to a host server for processing or storage or processed on the device 230'. A report 197, such as an acceptability report, can be displayed on the mobile device as shown. FIGS. 2E and 2F show examples of possible acceptability reports. These reports can be generated remotely using captured image data or on the mobile device.

As noted herein, glare, blur and other unwanted optical effects can interfere with a device's ability to resolve a barcode, an environmental monitor, or find the ellipses or other shapes used by a detection module to find the relevant locus for a given environmental monitor or other element on a label. In addition, activating a mobile device application and capturing video or a plurality of frames as stills or video is easier for a user than having to position a label relative to an overlay or use an external light source.

To help address these issues, in some embodiments, the image data can be collected as a plurality of frames, such as video for example, captured from device 230' as it moves along a suitable trajectory relative to the label. Thus, moving the device 230' from position A to B and from B back to A and/or moving the mobile device 230' from position C to D and/or moving the mobile device 230' back from position D to C, as indicated by the arrows in FIG. 2D, can be helpful. In addition, instructions for executing such a movement or movement pattern or an appropriate freeform movement of the mobile device, can be communicated to a user on the device's display. During the movement, multiple or continuous frames of image data can be collected from the label 297 and/or from the label 298 from various differing imaging angles. In one embodiment, the location (GPS, Wi-Fi, cellular, or otherwise) and phone number information of the mobile device 230' is transmitted using the mobile device 230' and, optionally, stored in a database with respect to one or more frames of image data or for each image data capture session. This information can be used in various reports and to confirm and/or record the device and location of a label processing event.

Capturing multiple frames of data can allow data frames with errors, such as high glares to be ignored. In addition, by time indexing frames and/or tracking accelerometer readings, using an accelerometer-equipped mobile device 230', or using other parameters, frames of image data can be differentially analyzed to better identify the elements on a label and better resolve readings. Also, correlations between image data frames can be used to effectively filter out glare or otherwise determine correlations that increase the accuracy of the algorithm, such as a detection module, executing on a server or the processing unit to accurately distinguish an environmental monitor from another region of a given label. For vials with curved surfaces, monitors with low intensity material but hard to read color changes, smeared barcodes, and other hard to resolve label elements, differential analysis and additional sets of data frames can improve the reading and processing of labels.

In addition, the flash can be triggered in all data frame captures or in some and not others such that an additional known change in the data set can be used to improve imaging accuracy. Similarly, when barcode or other symbols are used on the label, black and white regions (or other patterned or colored regions) can be used to evaluate the dynamic range of the image data captured by the camera, i.e. the limits of one or more of the various optical parameters that are exhibited by the particular captured image data set.

Special symbols can also be placed around monitors or other elements on which an algorithm can key to improve a detection process for a given element on the label or a reading process for a given label element. Examples of special symbols that can be employed include small L-shaped corner brackets that can provide a distinct image under a variety of lighting conditions and can demark an image area within which the algorithm can locate a monitor image, barcode image or other element image to be recognized. The mobile device can include information regarding possible images that may be present in the image data captured by the camera and which are to be recognized by, and can be accessed by the algorithm. In addition, an element on the label such as a barcode or a number can include information or index information in a database that specifies what other elements are on the same label and which positions should be interrogated to obtain an environmental exposure level in a given set of image data. Because the indicator, barcode, monitor have different appearance and optical properties that can all be individually identified, having additional data to process or ignore as well as making use of predetermined known features of a given label can facilitate image data processing that results in accurate acceptability reports.

In one embodiment, an application programming interface (API) is used to control or otherwise use the camera and/or the flash in the mobile device. Embodiments of image processing software according to the invention can modify the API or override it such that software modules pre-installed on the device to facilitate label 100 imaging and processing receive raw image data. By controlling the camera, application programming interface, or other software or hardware component used to control the camera, one embodiment of image processing software according to the invention prevents the image data captured using the camera from being pre-processed. For example, some mobile devices generally pre-process the image data in various ways, such as by performing a white balance filter or red eye reduction or other processing steps. The software described herein can override such preprocessing and permit acquisition of raw camera data. In this manner, the image data collected can be free of color correction modifications, and can include an indication of the exposure level of incoming light to the mobile device and the label under inspection. Under some circumstances, if image data pre-processing is not prevented, the application of a contrast, white balance, or other filter can result in errors when trying to identify or read an element on a given label, for example, an environmental monitors.

In order to quantify the colors of the reference zone, color reference zone, and active areas of a monitor, it may be necessary to calibrate the image with knowledge of the color values of black and white in the image. These values can be obtained by measuring the color values of the black and white components of the bar code. Other known or predetermined label components can also be so used.

As shown, in FIG. 2D, an imaging device such as a mobile device 230' has captured image data which has been processed to generate a report 197 which is displayed on the device. In one embodiment, this report can be an acceptability report. In another embodiment, report 197 can include any data suitable for populating a record management system generated during, or derived from, capturing and processing image data with respect to a product having a label. For example, the interactions and events that occur between a first entity and a second entity relative to a host product associated with a product label, such as label 297, can be tracked and recorded in one or more databases using a mobile device. The tracking and recording can be enabled by scanning a second label 298, associated with the second entity, which label 298 has one or more identifiers, monitors, text, authentication elements, and other elements as described herein.

In one embodiment, the report 197 can include medical data such as patient data. Thus, if the product label 297 was affixed to a vaccine vial, or other vaccine container, a record of a possible vaccination of the particular patient, can be generated as a result of the mobile device scanning the label and a patient identifier, such as from a second label 298 or object, as part of the image data capture shown in FIG. 2D. If the conditions of use are known, for example, a medical professional may be known to be performing the scanning in conjunction with the administration of the vaccine, the vaccination event can be recorded with a high degree of confidence. A data file can be pre-processed or analyzed using a rules engine or other logical system such that transactions are interpreted and routed to a database of a medical record management system, thus providing a record of the procedure for the patient. In this case, a patient identifier scanned in the same session as the scan of a vaccine container for the patient can be interpreted by the software to indicate that the patient was vaccinated. The date and location of the vaccination can automatically be generated using the time stamp of the mobile device and its GPS reading. Thus, an acceptability report can contain such transactional information as well as information revealed by the product label as to whether the associated host product is acceptable or unacceptable for use. Shipping and tracking information associated with the label 297 can also be included in the report 197 and can enhance the report with information regarding the start and end of the distribution itinerary for the host product bearing label 297 and. Shipping and tracking information can be supplied to the report 197 by a host server and/or by mobile device 230'. For example, mobile device 230' can provide delivery information derived from label 297 and/or label 298, which can optionally include addressee information derived from a patient identifier, a written address or another label element. If the user scans label 297 and/or label 298 just prior to a use of the host product mobile device 230' can also provide information as to the likely date of use and/or time of use provided by a date/time clock on mobile device 230' as well as location information if mobile device 230' has a GPS functionality or another location providing functionality. In another example, label 297 can be scanned to yield medical product serial number information and label 298 can be scanned to yield patient information enabling a host server to link the patient to that particular serialized medical product item.

Examples of acceptability reports are shown in FIGS. 2E and 3F. As shown in FIG. 2E, an acceptability report indicates that the product associated with the label may be used because the authenticity, environmental conditions, (in this case, temperature) and expiration date checks performed relative to the label were all marked to indicate they were within acceptable limits. In contrast, as shown in FIG. 2F, the acceptability report indicates that the product associated with the label with respect to which image data was captured should not be used. This conclusion and the associated instruction to the user ("Do Not Use Product") can be easily understood by the user because although the authenticity and expiration date checks are marked as acceptable, the temperature exposure as checked via one or more environmental monitors was marked to indicate it was not within acceptable limits. For example, if the product having the label was exposed to excessive heat or cold conditions or exposed to unsuitable conditions for too long, the indicator read from a monitor, the relevant monitor state reflects these events. In turn, the monitor image data provides evidence that a software application can interpret to make an acceptability decision.

Verification of acceptability of host products, e.g. biological pharmaceuticals, that have a preferred cold storage requirement, but that can be exposed at room temperature e.g. for transport, for a limited time period is possible using the software-based system described herein. The environmental monitor(s) may be responsive to different types of environmental stimuli. Examples of such stimuli can include, without limitation, cumulative temperature exposure, exposure to a temperature above a threshold, or exposure to a temperature below a threshold. For example, an environmental monitor that measures time above a threshold temperature can be used for verification of acceptability of host products, e.g. biological pharmaceuticals, that have a preferred cold storage requirement, but that can be exposed at room temperature e.g. for transport, for a predetermined time period. The image data associated with scanning such a label can be used to automatically identify the relevant environmental monitor and determine a color change indicative of whether or not such a predetermined time period has been exceeded.

Figure 3:
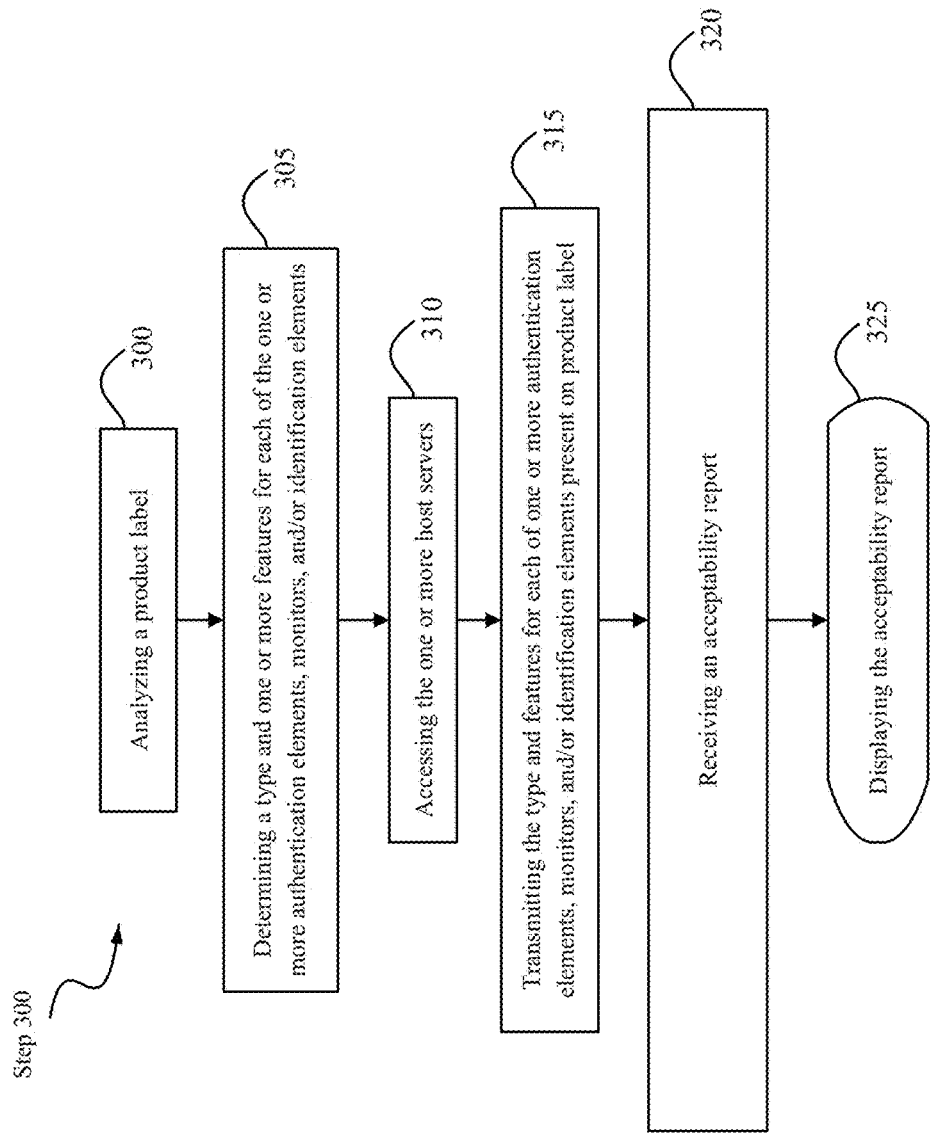
FIG. 3 illustrates a method according to one embodiment of the present invention.

As shown in FIG. 3 at step 300, in one embodiment of the present invention, an image capture and communication device may analyze a product label 100 (as shown in FIGS. 1, 2A, and 2B) for a host product. Based on its analysis, for example, by scanning for visual or electronic signals indicative of one or more authentication elements, monitors, and/or identification elements present on product label 100, the image capture and communication device determines a type and one or more features for each of the one or more authentication elements, monitors, and/or identification elements, as shown at step 305.

In one embodiment, the type of an authentication element, monitor, or identification elements indicates to the image capture and communication device how the image capture and communication device may retrieve data from the authentication element, monitor, or identification element. For example, the type of an identification element may be a one-dimensional barcode, which may indicate to the image capture and communication device to scan the barcode and interpret the barcode data. In another example, the type of a monitor may be an environmental monitor with an active zone and a reference zone, which may indicate to the image capture and communication device to capture an image of the two zones for comparison. In another example, the type of an authentication element may be RFID, which may indicate to the image capture and communication device to send an interrogation signal and retrieve the data from the RFID.

The one or more features for each of the one or more authentication elements, monitors, and/or identification elements are features associated with the type of authentication element, monitor, and identification element that are used to provide data stored in the authentication element, monitor, and identification element. For example, if the type of identification element is a one-dimensional barcode, the features may be the lines and/or numbers associated with the barcode. In another example, if the type of monitor is an environmental monitor that includes an active zone and a reference zone, the features of the monitor may be the color of the active zone and the color of the reference zone. In another example, if the type of authentication element is RFID, the features of the authentication element may be the data stored in the RFID.

As further shown in FIG. 3 at step 310 according to one embodiment of the present invention, the image capture and communication device may access the one or more host servers 190 (as shown in FIG. 1). The image capture and communication device may accomplish such access by connecting to host servers 190 through network 185 (as shown in FIG. 1) and/or cellular network 180 (as shown in FIG. 1). In other embodiments, the image capture and communication device may connect to host servers 190 through a direct satellite link. Once the image capture and communication device is either directly or indirectly connected to the host server, the image capture and communication device may transmit the type and features for each of one or more authentication elements, monitors, and/or identification elements present on product label 100, as shown at step 315. The image capture and communication device may transmit the type and features to the host servers 190 (as shown in FIG. 1) via short message service (SMS) text message, TCP/IP messaging, email, FTP, PIN email, and/or instant message.

The image capture and communication device may receive an acceptability report from host servers 190 (as shown in FIG. 1) based on the type and features for each of one or more authentication elements, monitors, and/or identification elements present on product label 100, as shown at step 320. The image capture and communication device may receive the acceptability report from host servers 190 (as shown in FIG. 1) via SMS text message, TCP/IP messaging, email, FTP, PIN email, and/or instant message. In further embodiments, the image capture and communication device may receive the acceptability report from the host servers 190 (as shown in FIG. 1) by the host servers 190 providing a uniform resource locator (URL) to a website for the image capture and communication device to access through cellular network 180 (as shown in FIG. 1) or network 185 (as shown in FIG. 1). In such embodiments, host servers 190 (as shown in FIG. 1) post the acceptability report to the website available at the URL.

As further shown in FIG. 3 at step 325 according to one embodiment of the present invention, the image capture and communication device may display the acceptability report. For example, image capture and communication devices 170, 160, and/or 110 may output a text-based and/or graphical-based acceptability report on display devices such as a liquid crystal display (LCD), light emitting diode (LED) display, or cathode ray tube (CRT) display.

The acceptability report may include text, symbols, and/or graphics indicating any of the following: whether the host product is acceptable to use, whether the host product is authentic; product identification data; product history data, including the environmental history of the host product; instructions on how the user should proceed based on the host product's acceptability; pedigree detail, such as, a SGTIN and/or pedigree verification; and whether a new expiration or use-by date is provided based on the environmental exposure. If the host product is a pharmaceutical product, a link to download a patient information sheet may be included. In addition, late breaking warnings as to possible adverse reactions, product recall information, directions, or requests, or a link to such information, may also be included in the report. The acceptability report may include a link for the holder of the host product to re-order or return the host product. Such information may be triggered by data received from the one or more authentication elements, monitors, and/or identification elements.

The acceptability report may be output audibly by the image capture and communication device. For example, the image capture and communication device may use text-to-speech routines or speech libraries located on either the host servers or image capture and communication device. Such embodiments may help vision-impaired users understand whether a host product is acceptable to use.

Figure 4:
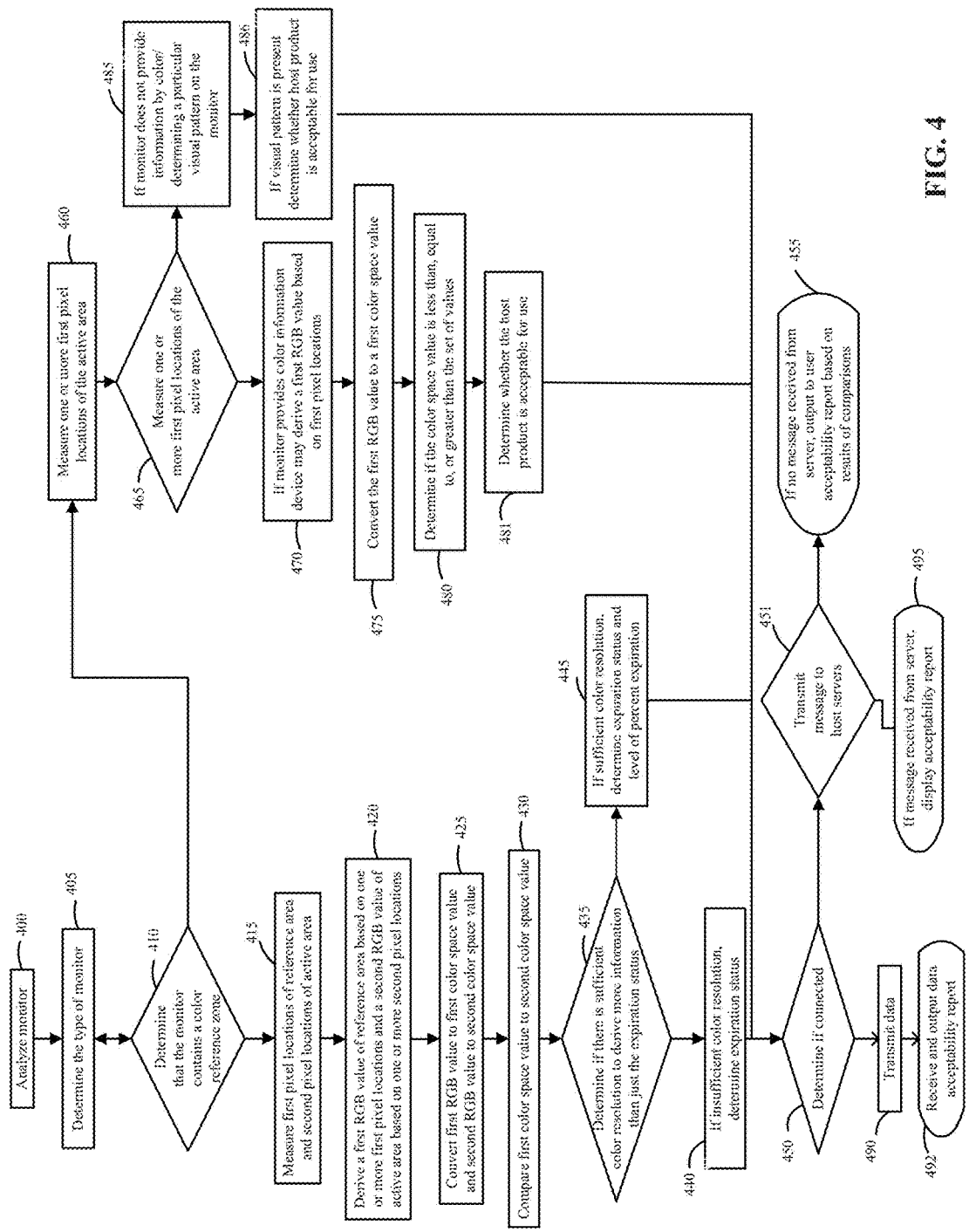
FIG. 4 illustrates a method according to another embodiment of the present invention.

As shown in FIG. 4 at step 400, according to one embodiment of the present invention, one or more image capture and communication devices 170, 160, and 110 (as shown in FIG. 1) may analyze a monitor with a type and one or more features based on the type for a host product. The one or more image capture and communication devices may take a still picture or image of the monitor. At step 405, the one or more image capture and communications devices may determine the type of monitor and the one or more features based on the type. At step 410, the one or more image capture and communication devices may determine whether the one or more features and/or type indicate that the monitor contains a color reference zone, which has a reference area and an active area, such as are included in monitor 210 (as shown in FIG. 2A).

If the features and/or type indicate that the monitor contains a color reference zone, at step 415, the one or more image capture and communication devices may measure one or more first pixel locations of the reference area or reference color area on the label or as part of the monitor and one or more second pixel locations of the active area. In one embodiment, the measuring at step 415 is done through executing pattern recognition routines. At step 420, the one or more image capture and communication devices may derive a first RGB value of the reference area or reference color area based on the one or more first pixel locations and a second RGB value of the active area based on the one or more second pixel locations. At step 425, the one or more image capture and communication devices may convert the first RGB value to a first color space value and the second RGB value to a second color space value. At step 430, the one or more image capture and communication devices may compare the first color space value to the second color space value. For example, color space values may be grayscale, which is obtained by calculating the average of the RGB values. Another color space value example may be cyan OD, which can be obtained by calculating the negative of the logarithm to the base 10 of the R value expressed as a fraction of its full-scale value.

At step 435, the one or more image capture and communication devices may determine whether, for example, the still image or picture contains sufficient color resolution for the one or more image capture and communication devices or the one or more host servers 190 (as shown in FIG. 1) to derive color space values accurate enough to provide all available product information from the monitor. For instance, it is possible that if the lighting conditions are poor and the an image capture or communication device may not have created enough light, the image capture and communication device may still have retrieved sufficient data to determine whether the active zone is darker or lighter than the reference zone, but not sufficient data to accurately determine the degree of darkness and lightness necessary to derive more data from the comparison.

Thus, if the one or more image capture and communication devices determine that the still image or picture does not contain sufficient color resolution, at step 440, the one or more image capture and communication devices may determine whether, based on that comparison (at step 430), the host product is acceptable for use. In further embodiments, because of the lack of sufficient color, any acceptability data generated downstream may indicate whether the host product is acceptable, but may not accurately indicate the degree of acceptability, for example, the degree of exposure to a particular condition. In such an embodiment, the degrees of acceptability may be omitted from acceptability reports.

In one embodiment, if the color resolution at step 440 is not sufficient to obtain an accurate color measurement and accurate determination of the degree of acceptability, it may still be sufficient to place the color value in a region of acceptability. For example, in one embodiment four regions of environmental exposure can be defined, with boundaries at 0%, 25%, 50%, 75%, and 100% of permissible environmental exposure. Other examples can employ a different number of exposure regions and different permissible boundaries. The color measurement may have sufficient accuracy and resolution to determine in which of the regions the exposure occurs. These regions can in turn be used to calculate whether or not the environmental exposure of a given label and associated product warrant that it can be reported as acceptable for use or require it to be reported as unacceptable for use.

If the one or more image capture and communication devices determine that the still image or picture does contain sufficient color resolution, at step 445, the one or more image capture and communication devices may determine whether, based on that comparison (at step 430), the host product is acceptable for use and may indicate the degree of acceptability of use in any acceptability report generated downstream. In one embodiment if the active zone's color may darken in response to cumulative temperature exposure over time outside of acceptable limits for the host product. If the active zone's color is as dark as or darker than reference zone, the monitor may be indicating by visual signal that the host product with which it is associated is no longer acceptable for use. In another embodiment, the active zone's color may lighten in response to cumulative temperature exposure over time outside of acceptable limits for the host product. In such embodiments, if the active zone's color is lighter than reference zone's color, the monitor may be indicating by visual signal that the host product with which it is associated is no longer acceptable for use.

If, at step 410, the one or more image capture and communication devices determines that the features and/or type indicate that the monitor does not contain a color reference zone, at step 460, the one or more image capture and communication devices may measure one or more first pixel or color locations of the active area. In one embodiment, the measuring at step 460 is done through executing pattern recognition routines. At step 465, the one or more image capture and communication devices determines, based on the type and/or features of the monitor, whether the monitor provides information, such as environmental condition, by color. If the monitor provides information by color, at step 470, the one or more image capture and communication devices may derive a first RGB value of the active area based on the one or more first pixel or color locations. At step 475, the one or more image capture and communication devices may convert the first RGB value to a first color space value. At step 480, the one or more image capture and communication devices may compare the first color space value to a set of values based on the type and/or features of the monitor in order to determine if the color space value is less than, equal to, or greater than the set of values. Based on the comparison (at step 480), the one or more image capture and communication devices, at step 481, may determine whether the host product is acceptable for use.

If the monitor does not provide information by color, at step 485, the one or more image capture and communication devices determines whether information is provided by determining a particular visual pattern on the monitor. For example, in one embodiment, if certain environmental conditions are present, a symbol may appear in the active area, such as a check mark as shown in monitor 225 in FIG. 2A. At step 486, if the visual pattern is present on the monitor, the one or more image capture and communication devices may determine, based on the visual pattern, whether the host product is acceptable for use. Depending on the type and features of the monitor, the existence of a visual pattern may indicate that a host product is or is not acceptable for use; or, the visual pattern may need to be interpreted in light of other data, such as other data from other monitors, authentication elements, and/or identity elements, in order for the image capture and communication device and/or host servers to determine whether the host product is acceptable for use.

At step 450, the one or more image capture and communication devices determines whether the image capture and communication device is directly or indirectly connected to one or more host servers 190 (as shown in FIG. 1) through network 185 (as shown in FIG. 1). If the one or more image capture and communication devices determines that it is connected to one or more host servers through network 185, the image capture and communication device may, at step 490, transmit data including the type, features, comparison results (at steps 430 and/or 480), and/or determination results (at steps 435, 440, 481, and/or 486) to the one or more host servers. At step 492, the image capture and communication device may receive data from the host server that is associated with the one or more host product that is associated with the monitor and output the data in the form of an acceptability report (as described in step 325 in FIG. 3). Such data may include the host product's name, strength, presentation (for example, pre-filled syringe, vial, ampoule, etc.), quantity, product identification number, serialized numeric identifier (SNI), SGTIN, numeric drug code (NDC), lot number, expiration date, location of manufacture, date of manufacture, storage conditions, date/time and condition of unit from each reading including identification, authentication and monitor, site of reading or GPS information, identity of reading device or person or entity making the reading, product specific information (for example, specifications, package insert, use instructions, etc.), recall status, warranty information, product coupons for discounts, notice of product status change (for example, if the product is subject to a recall or other action, notice could be automatically sent to the last entity reading the acceptability device), notice to reorder product, information and emergency call or e-mail addresses.

If the one or more image capture and communication devices determine that it is not connected to one or more host servers through network 185, at step 451, the one or more image capture and communication devices determine whether they can transmit a message, such as SMS, through cellular network 180 to the one or more host servers. If the one or more image capture and communication devices determine that they can transmit a message, at step 495, the one or more image capture and communication devices may receive data from the host server that is associated with the one or more host products that are associated with the monitor. In one embodiment, the data may be in the form of a link, such as a URL, that references a webpage that hosts an acceptability report that the one or more host servers have generated (as described in step 325 in FIG. 3).

If the one or more image capture and communication devices determine that they cannot transmit a message, at step 455, the one or more image capture and communication devices may output to the user an acceptability report based on the results of the comparisons and determinations at steps 430, 435, 440, 480, 481, and/or 486. The output may be in the form of a visual display and/or audible display.

Figure 5:
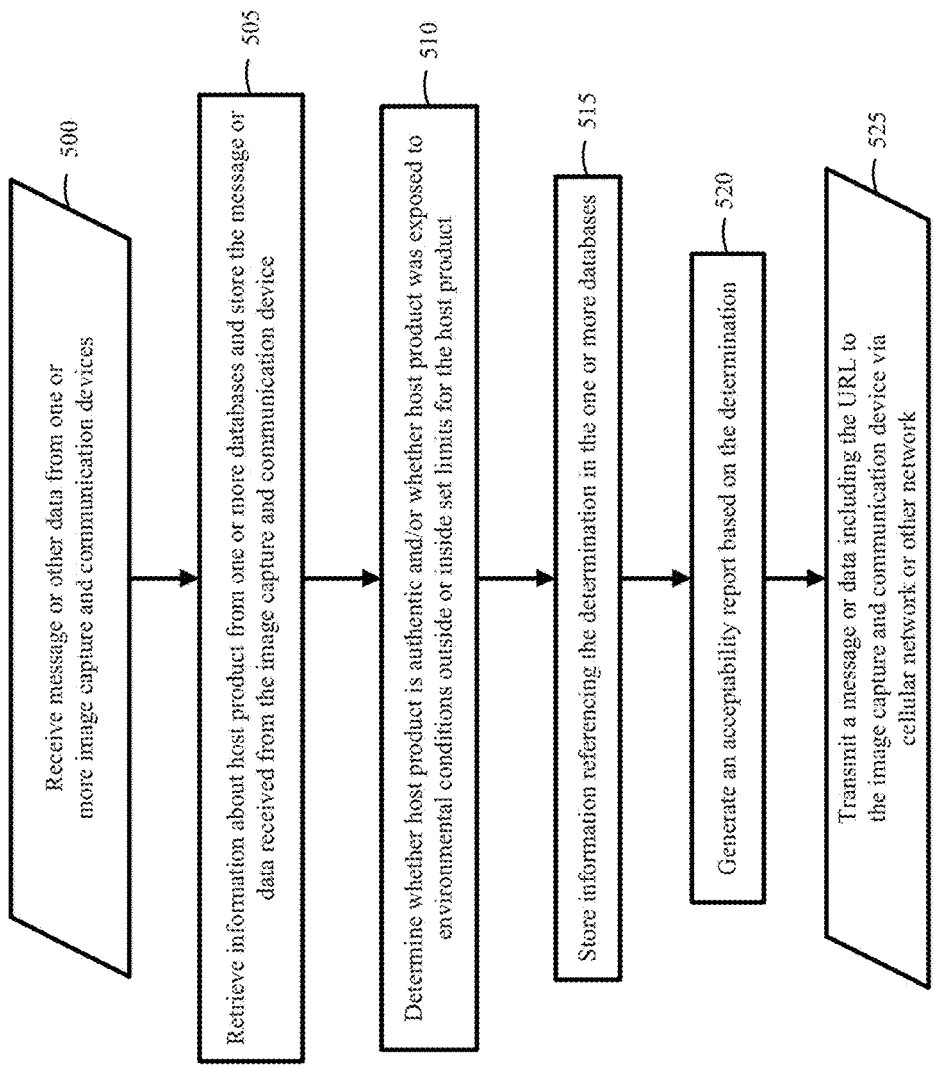
FIG. 5 illustrates a method according to another embodiment of the present invention.

As shown in FIG. 5 at step 500, in one embodiment of the present invention, one or more host servers 190 (as shown in FIG. 1) may receive a message or other data from one or more image capture and communication devices 170, 160, and 110 (as shown in FIG. 1) including the type and features of each of the one or more authentication elements, monitors, and/or identification elements present on the product label that the image capture and communication device 170, 160, and 110 analyzes. In further embodiments, message or data is received via SMS text message, TCP/IP messaging, email, FTP, PIN email, and/or instant message.

As further shown in FIG. 5 at step 505, based on the message or data, the host servers 190 (as shown in FIG. 1) retrieve information about the host product from one or more databases 195 (as shown in FIG. 1) and store the message or data that was received from the image capture and communication device 170, 160, and 110 (as shown in FIG. 1) in databases 195. Information about the host product may include the host product's name, strength, presentation (for example, pre-filled syringe, vial, ampoule, etc.), quantity, product identification number, SNI, SGTIN, NDC, lot number, expiration date, location of manufacture, date of manufacture, storage conditions, date/time and condition of unit from each reading including identification, authentication and monitor, site of reading or GPS information, identity of reading device or person or entity making the reading, product specific information (for example, specifications, package insert, use instructions, etc.), recall status, warranty information, product coupons for discounts, notice of product status change (for example, if the product is subject to a recall or other action, notice could be automatically sent to the last entity reading the acceptability device), notice to reorder product, information and emergency call or e-mail addresses.

In further embodiments, at step 510, based on the message or data, the host server 190 (as shown in FIG. 1) may determine, for example, whether the host product is authentic and/or whether the host product was exposed to environmental conditions outside or inside set limits for the host product. At step 515 one or more host servers 190 (as shown in FIG. 1) may store information referencing the determination (made at step 510) in the one or more databases 195 (as shown in FIG. 1) 515. At step 520, host servers 190 (as shown in FIG. 1) may generate an acceptability report based on the determination (made at step 510). In one embodiment, generating an acceptability report (generated at step 520) may include generating an HTML-based webpage and a URL pointing to the webpage. At step 525, the host servers 190 (as shown in FIG. 1) may transmit a message or data including the URL to the image capture and communication device via cellular network 180 (as shown in FIG. 1) or network 185 (as shown in FIG. 1).

In another embodiment, generating an acceptability report (generated at step 520) may include tabulating data based on the determination (made at step 510) and/or other attributes of the host product. In such an embodiment, at step 525, one or more host servers 190 (as shown in FIG. 1) may transmit the acceptability report in the form of such tabulated data to the image capture and communication device 170, 160, and/or 110 (as shown in FIG. 1) via SMS text message, TCP/IP messaging, email, FTP, PIN email, and/or instant message.

Figure 6A:
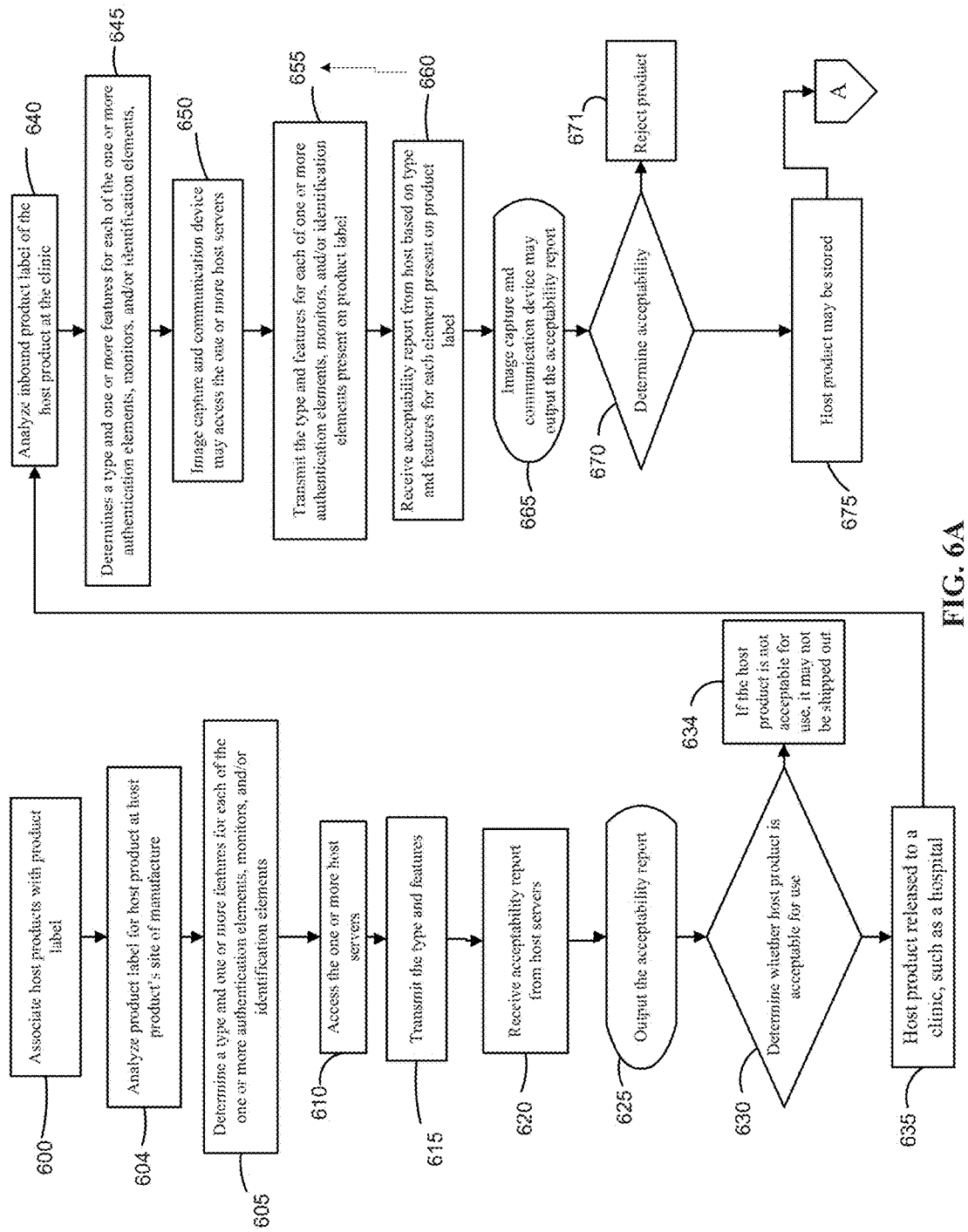
FIG. 6A illustrates a method according to another embodiment of the present invention.
Figure 6B:
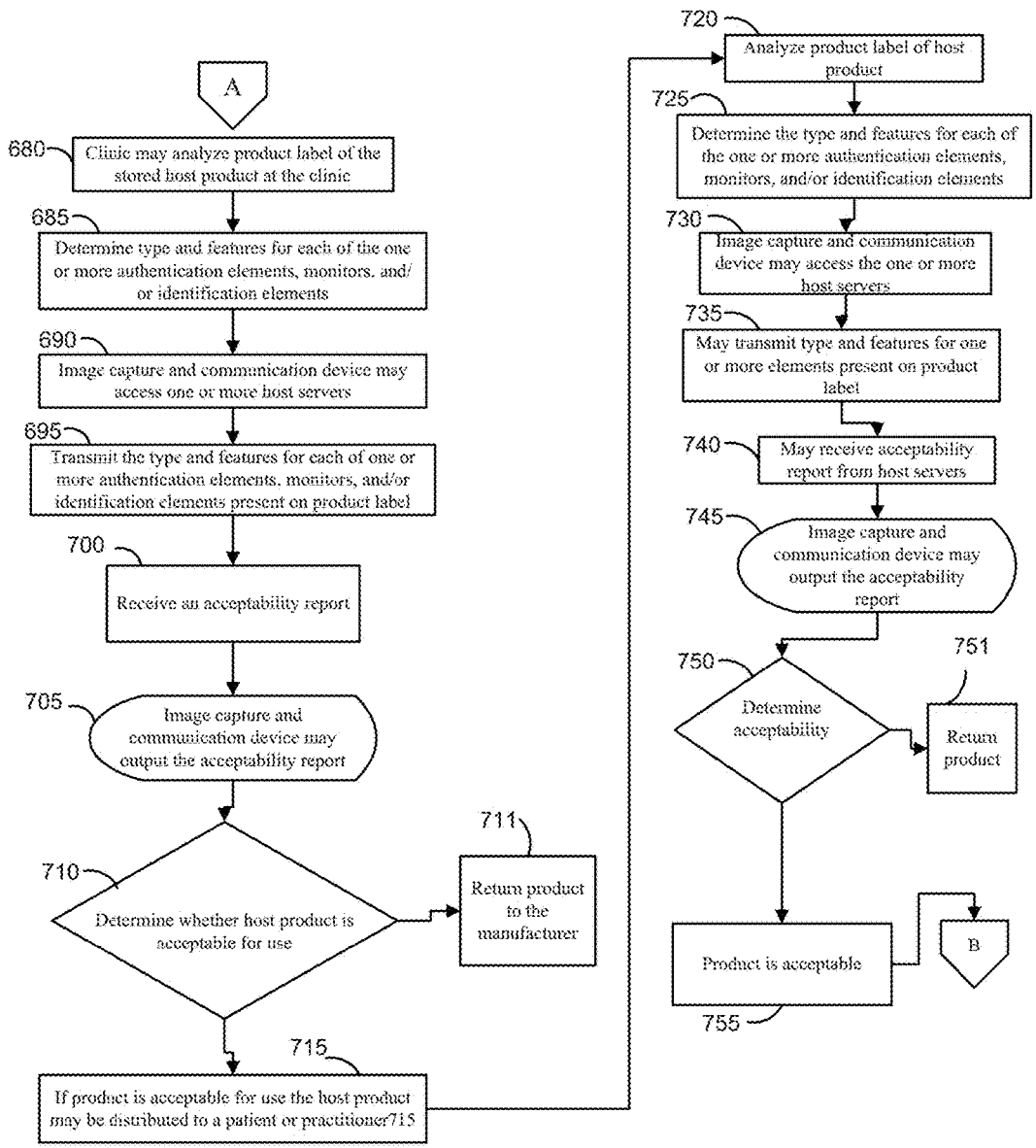
FIG. 6B illustrates a method according to another embodiment of the present invention.
Figure 6C:
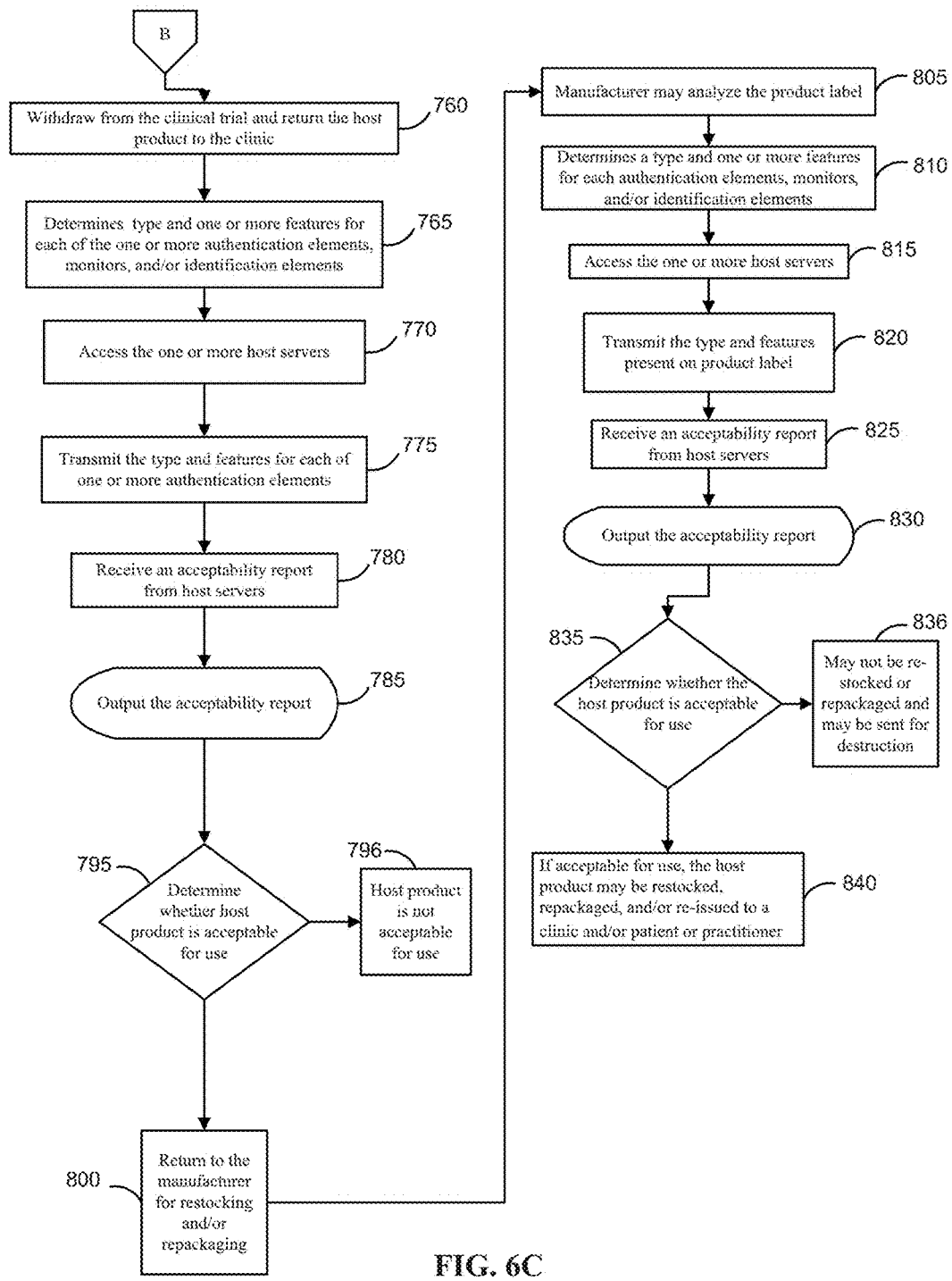
FIG. 6C illustrates a method according to another embodiment of the present invention.
Figure 7A:
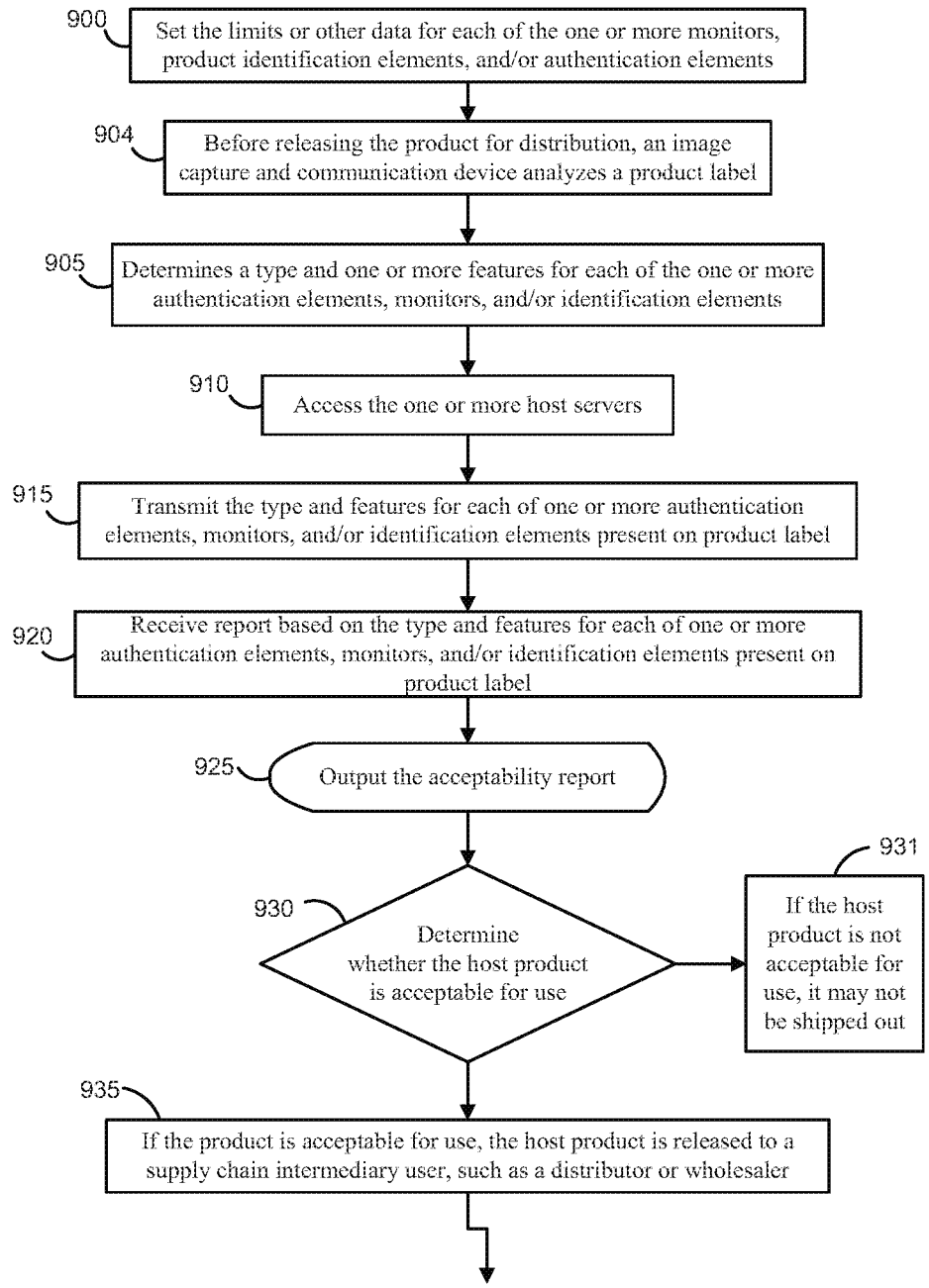
FIGS. 7A and 7B illustrate a method according to another embodiment of the present invention.
Figure 7B:
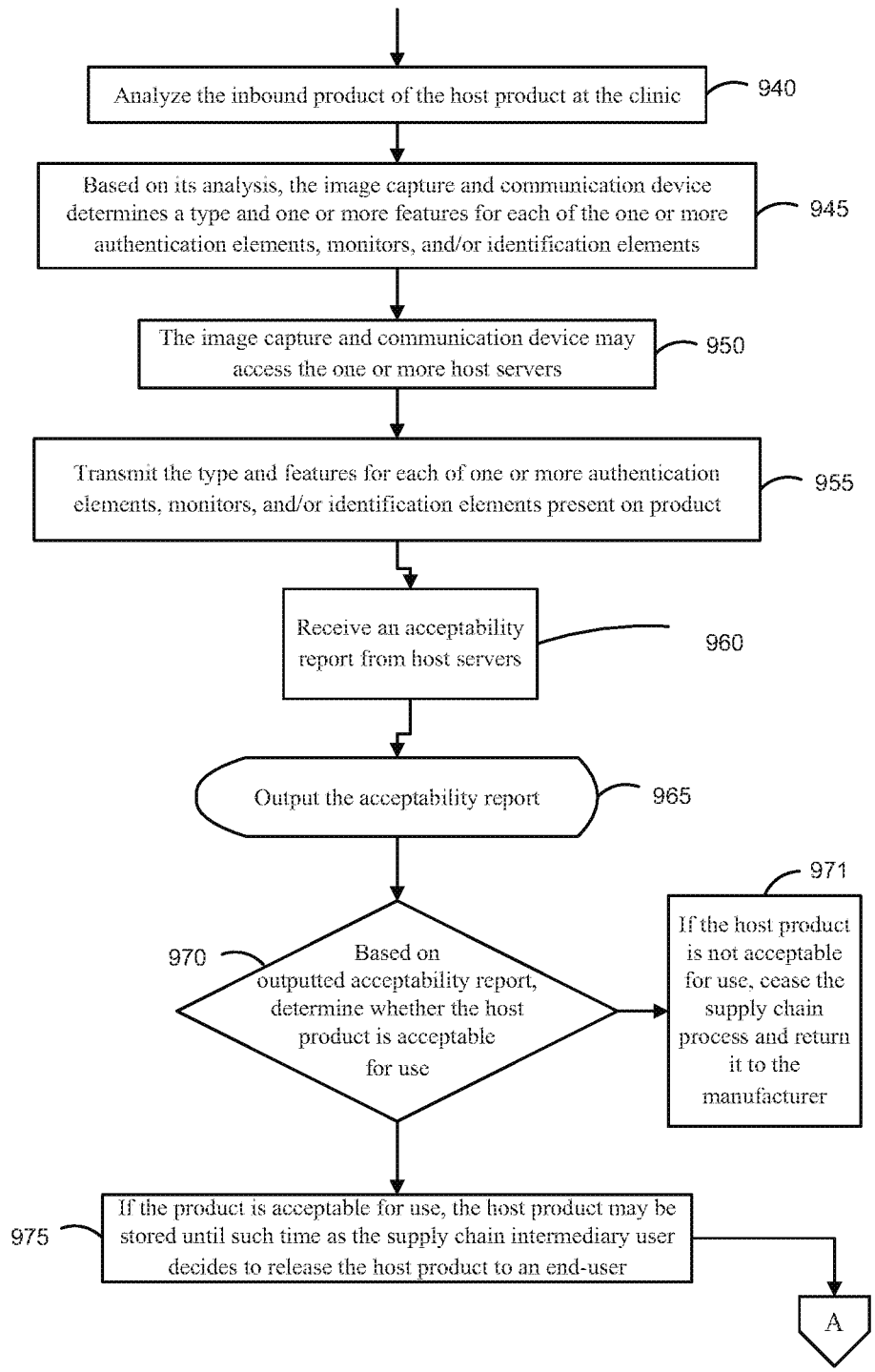
Figure 7C:
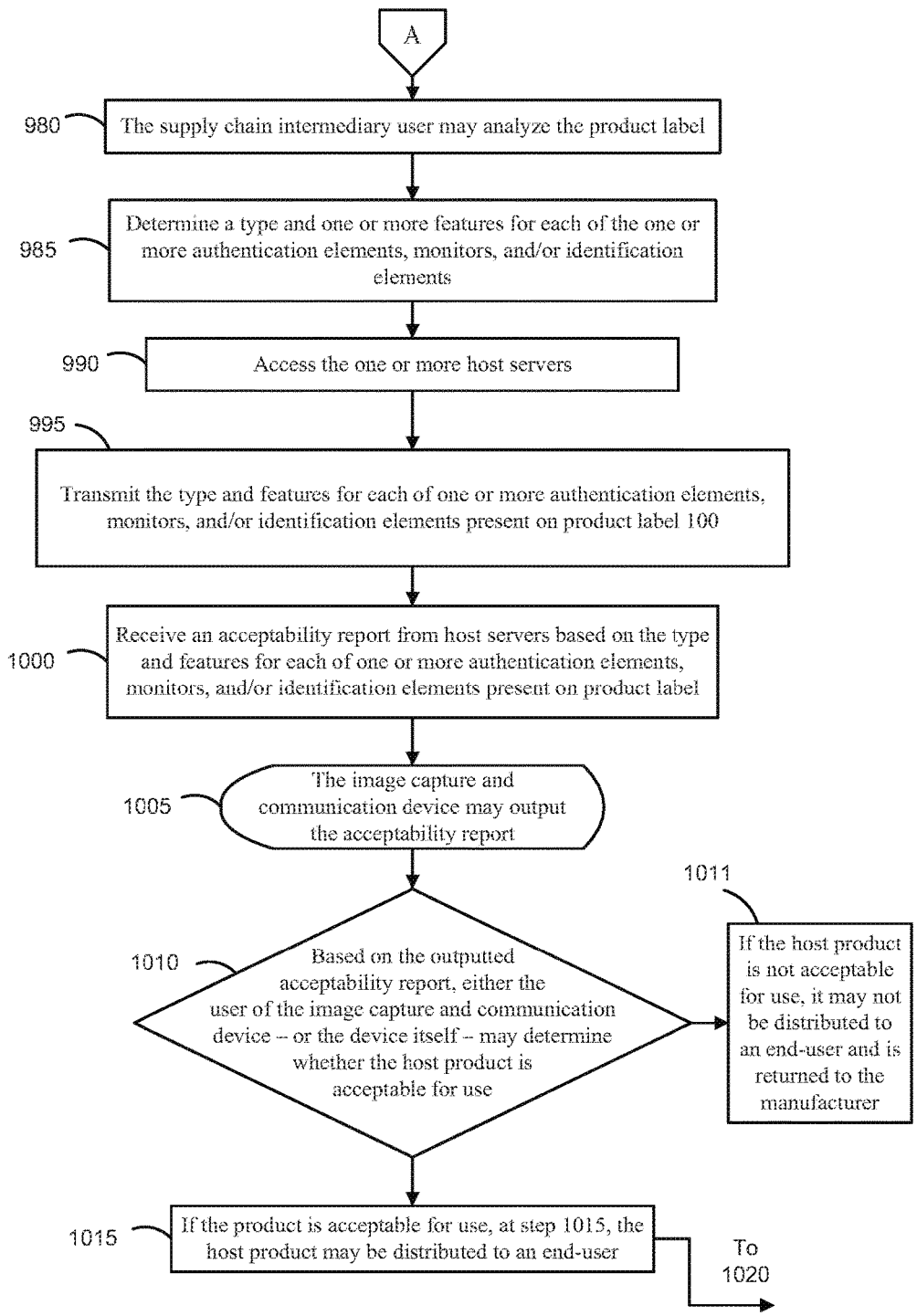
FIGS. 7C and 7D illustrate a method according to another embodiment of the present invention.
Figure 7D:
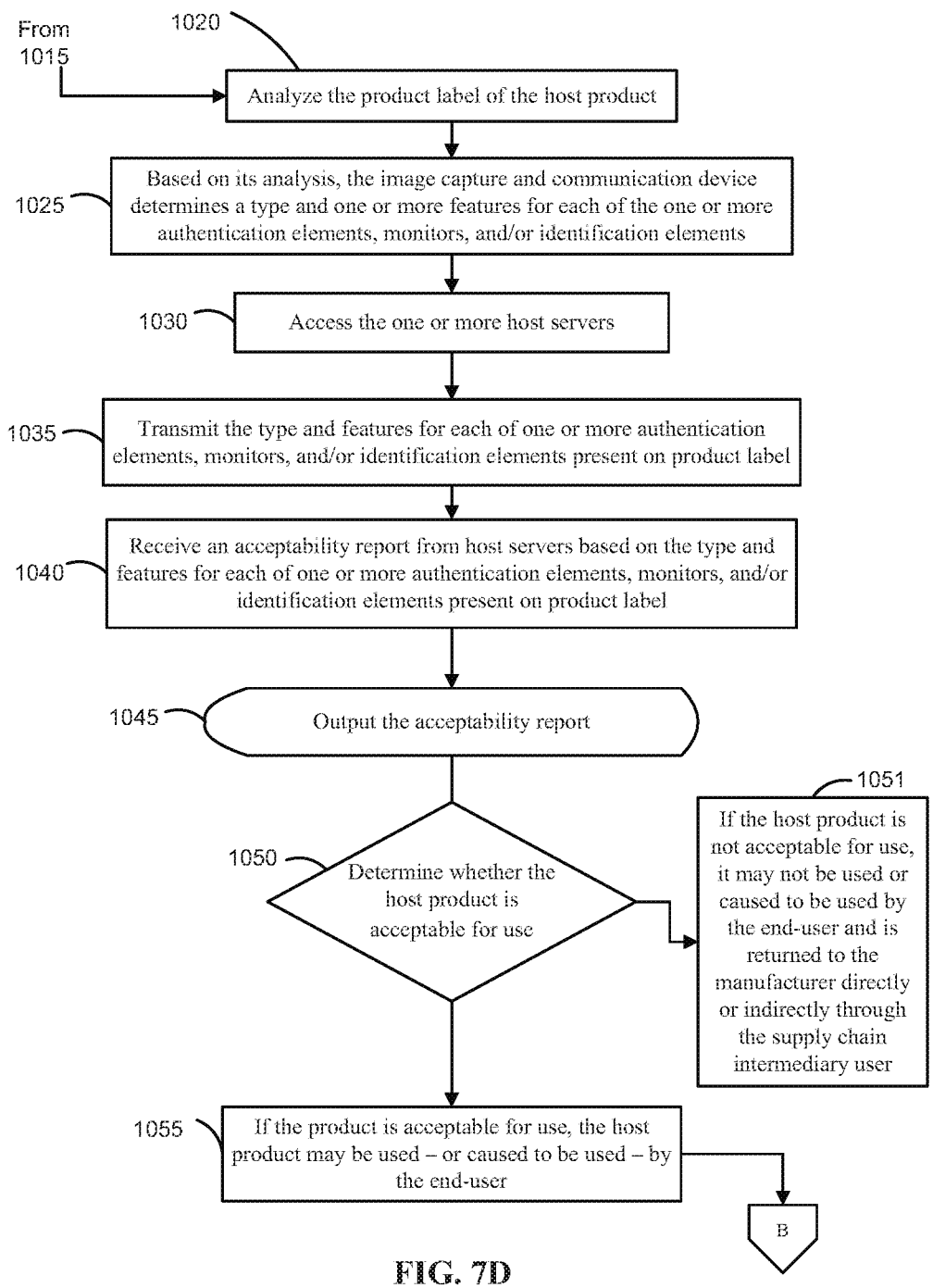
Figure 7E:
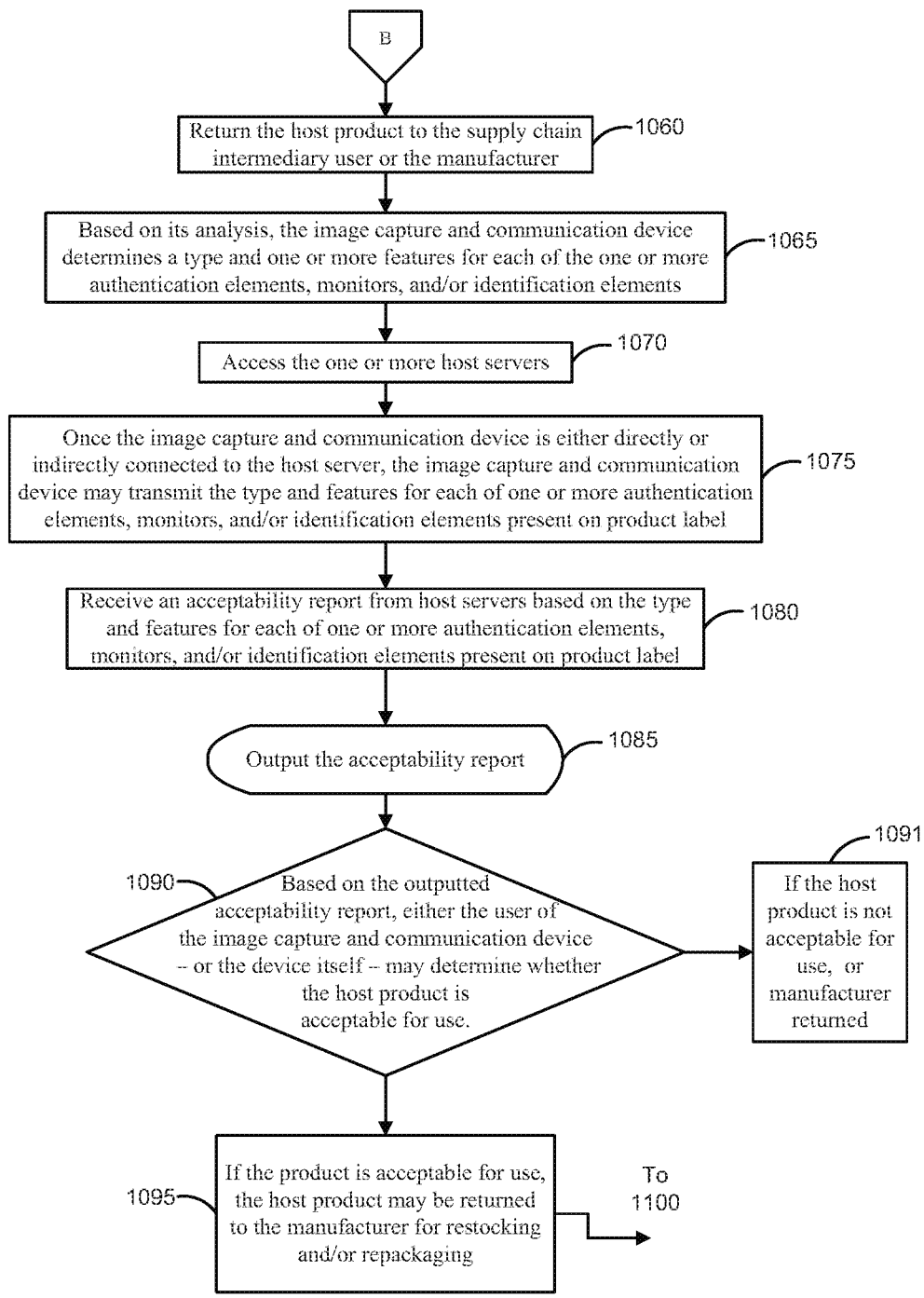
FIGS. 7E and 7F illustrate a method according to another embodiment of the present invention.
Figure 7F:
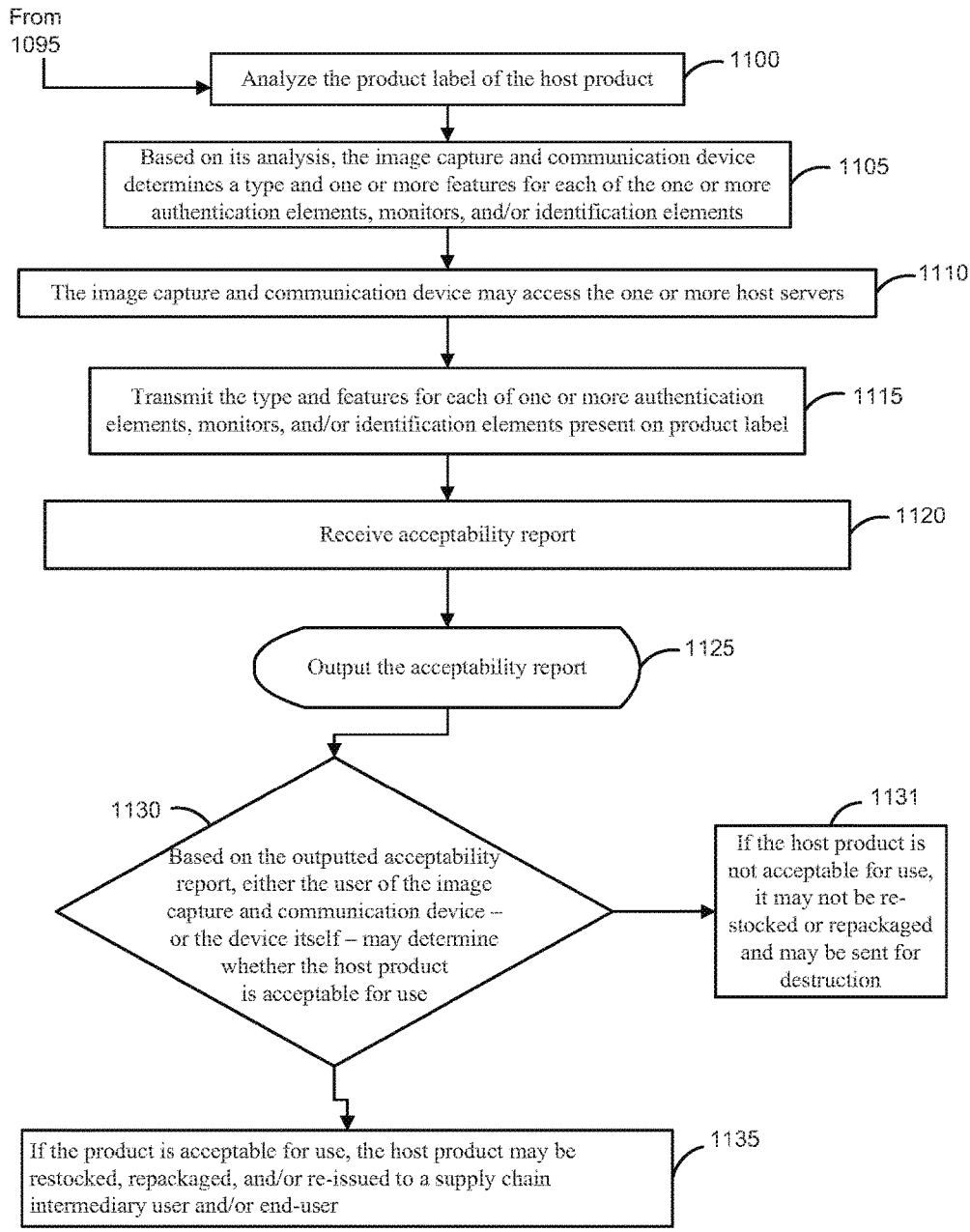

As shown in FIGS. 6A, 6B, and 6C, according to one embodiment of the present invention a manufacturer of a host product may use systems and methods of the present invention to track the acceptability of the host product throughout the steps of clinical trials of the host product. For example, at step 600, the manufacturer may associate one or more host products with a product label 100 (as shown in FIGS. 1, 2A, and 2B) including at least two of one or more monitors, product identification elements, and authentication elements. During the association (at step 600), the manufacturer may set the limits or other data for each of the one or more monitors, product identification elements, and/or authentication elements; or, the manufacturer may use one or more monitors, product identification elements, and/or authentication elements with pre-set limits and/or data as appropriate for the particular host product.

At step 604, before the manufacturer is ready to release the product for use at a clinical trial, an image capture and communication device may analyze a product label 100 (as shown in FIGS. 1, 2A, and 2B) for a host product at the host product's site of manufacture. Based on its analysis, for example, by scanning for visual or electronic signals indicative of one or more authentication elements, monitors, and/or identification elements present on product label 100, the image capture and communication device determines a type and one or more features for each of the one or more authentication elements, monitors, and/or identification elements, as shown at step 605.

At step 610, the image capture and communication device may access the one or more host servers 190 (as shown in FIG. 1). The image capture and communication device may accomplish such access by connecting to host servers 190 through network 185 (as shown in FIG. 1) and/or cellular network 180 (as shown in FIG. 1). In other embodiments, the image capture and communication device may connect to host servers 190 through a direct satellite link. Once the image capture and communication device is either directly or indirectly connected to the host server, the image capture and communication device may transmit the type and features for each of one or more authentication elements, monitors, and/or identification elements present on product label 100, as shown at step 615. The image capture and communication device may transmit the type and features to the host servers 190 (as shown in FIG. 1) via short message service (SMS) text message, TCP/IP messaging, email, FTP, PIN email, and/or instant message.

Further, the image capture and communication device may receive an acceptability report from host servers 190 (as shown in FIG. 1) based on the type and features for each of one or more authentication elements, monitors, and/or identification elements present on product label 100, as shown at step 620. The image capture and communication device may receive the acceptability report from host servers 190 (as shown in FIG. 1) via SMS text message, TCP/IP messaging, email, FTP, PIN email, and/or instant message. In further embodiments, the image capture and communication device may receive the acceptability report from the host servers 190 (as shown in FIG. 1) by the host servers 190 providing a uniform resource locator (URL) to a website for the image capture and communication device to access through cellular network 180 (as shown in FIG. 1) or network 185 (as shown in FIG. 1). In such embodiments, host servers 190 (as shown in FIG. 1) post the acceptability report to the website available at the URL.

At step 625 according to one embodiment of the present invention, the image capture and communication device may output the acceptability report. For example, image capture and communication devices 170, 160, and/or 110 may output a text-based and/or graphical-based acceptability report on display devices such as a LCD display, LED display, or CRT display. In addition, an audible report may be output in lieu of—or in addition to—the graphically displayed report. At step 630, based on the outputted acceptability report, either the user of the image capture and communication device—or the device itself—may determine whether the host product is acceptable for use. For example, the acceptability report may actually state "it is not acceptable for use" or "it is acceptable use" or provide certain data for interpretation by its user or the device/host servers itself/themselves. At step 634, if the host product is not acceptable for use, it may not be shipped out. In a further embodiment, the acceptability report may include instructions transmitted or generated by the manufacturer about what the user should do with an unacceptable product. If the product is acceptable for use, at step 635, the host product is released to a clinic, such as a hospital.

At step 640, the clinic and/or delivery driver may analyze the inbound product label 100 (as shown in FIGS. 1, 2A, and 2B) of the host product at the clinic. Based on its analysis, the image capture and communication device determines a type and one or more features for each of the one or more authentication elements, monitors, and/or identification elements, as shown at step 645.

At step 650, the image capture and communication device may access the one or more host servers 190 (as shown in FIG. 1). Once the image capture and communication device is either directly or indirectly connected to the host server, the image capture and communication device may transmit the type and features for each of one or more authentication elements, monitors, and/or identification elements present on product label 100, as shown at step 655. The image capture and communication device may receive an acceptability report from host servers 190 (as shown in FIG. 1) based on the type and features for each of one or more authentication elements, monitors, and/or identification elements present on product label 100, as shown at step 660. In addition, the acceptability report may also take into account historical information about the host product, including the data collected at the site of manufacture. The image capture and communication device may receive the acceptability report from host servers 190 (as shown in FIG. 1) via SMS text message, TCP/IP messaging, email, FTP, PIN email, and/or instant message. In further embodiments, the image capture and communication device may receive the acceptability report from the host servers 190 (as shown in FIG. 1) by the host servers 190 providing a uniform resource locator (URL) to a web site for the image capture and communication device to access through cellular network 180 (as shown in FIG. 1) or network 185 (as shown in FIG. 1). In such embodiments, host servers 190 (as shown in FIG. 1) post the acceptability report to the website available at the URL.

At step 665, the image capture and communication device may output the acceptability report. At step 670, based on the outputted acceptability report, either the user of the image capture and communication device—or the device itself—may determine whether the host product is acceptable for use. At step 671, if the host product is not acceptable for use, it may not be shipped out and returned to the manufacturer. In a further embodiment, the acceptability report may include instructions transmitted or generated by the manufacturer about what the clinic should do with an unacceptable product. If the product is acceptable for use, at step 675, the host product may be stored until such time as the clinic decides to release the host product to a patient or practitioner.

At step 680, the clinic may analyze the product label 100 (as shown in FIGS. 1, 2A, and 2B) of the stored host product at the clinic. Based on its analysis, the image capture and communication device determines a type and one or more features for each of the one or more authentication elements, monitors, and/or identification elements, as shown at step 685.

At step 690, the image capture and communication device may access the one or more host servers 190 (as shown in FIG. 1). Once the image capture and communication device is either directly or indirectly connected to the host server, the image capture and communication device may transmit the type and features for each of one or more authentication elements, monitors, and/or identification elements present on product label 100, as shown at step 695. The image capture and communication device may receive an acceptability report from host servers 190 (as shown in FIG. 1) based on the type and features for each of one or more authentication elements, monitors, and/or identification elements present on product label 100, as shown at step 700. In addition, the acceptability report may also take into account historical information about the host product, including the data collected at the site of manufacture and inbound at the clinic. The image capture and communication device may receive the acceptability report from host servers 190 (as shown in FIG. 1) via SMS text message, TCP/IP messaging, email, FTP, PIN email, and/or instant message. In further embodiments, the image capture and communication device may receive the acceptability report from the host servers 190 (as shown in FIG. 1) by the host servers 190 providing a uniform resource locator (URL) to a website for the image capture and communication device to access through cellular network 180 (as shown in FIG. 1) or network 185 (as shown in FIG. 1). In such embodiments, host servers 190 (as shown in FIG. 1) post the acceptability report to the website available at the URL.

At step 705, the image capture and communication device may output the acceptability report. At step 710, based on the outputted acceptability report, either the user of the image capture and communication device—or the device itself—may determine whether the host product is acceptable for use. At step 711, if the host product is not acceptable for use, it may not be distributed to a patient or practitioner for use in the trial and is returned to the manufacturer. In a further embodiment, the acceptability report may include instructions transmitted or generated by the manufacturer about what the clinic should do with an unacceptable product. If the product is acceptable for use, at step 715, the host product may be distributed to a patient or practitioner.

At step 720, the patient or practitioner may analyze the product label 100 (as shown in FIGS. 1, 2A, and 2B) of the host product at the practitioner's office, patient's home, or other place where the host product is administered to the patient. Based on its analysis, the image capture and communication device determines a type and one or more features for each of the one or more authentication elements, monitors, and/or identification elements, as shown at step 725.

At step 730, the image capture and communication device may access the one or more host servers 190 (as shown in FIG. 1). Once the image capture and communication device is either directly or indirectly connected to the host server, the image capture and communication device may transmit the type and features for each of one or more authentication elements, monitors, and/or identification elements present on product label 100, as shown at step 735. The image capture and communication device may receive an acceptability report from host servers 190 (as shown in FIG. 1) based on the type and features for each of one or more authentication elements, monitors, and/or identification elements present on product label 100, as shown at step 740. In addition, the acceptability report may also take into account historical information about the host product, including the data collected at the site of manufacture and inbound and outbound at the clinic. The image capture and communication device may receive the acceptability report from host servers 190 (as shown in FIG. 1) via SMS text message, TCP/IP messaging, email, FTP, PIN email, and/or instant message. In further embodiments, the image capture and communication device may receive the acceptability report from the host servers 190 (as shown in FIG. 1) by the host servers 190 providing a uniform resource locator (URL) to a website for the image capture and communication device to access through cellular network 180 (as shown in FIG. 1) or network 185 (as shown in FIG. 1). In such embodiments, host servers 190 (as shown in FIG. 1) post the acceptability report to the website available at the URL.

At step 745, the image capture and communication device may output the acceptability report. At step 750, based on the outputted acceptability report, either the user of the image capture and communication device—or the device itself—may determine whether the host product is acceptable for use. At step 751, if the host product is not acceptable for use, it may not be used or caused to be used by a patient or practitioner in the trial and is returned to the manufacturer. In a further embodiment, the acceptability report may include instructions transmitted or generated by the manufacturer about what the clinic should do with an unacceptable product. If the product is acceptable for use, at step 755, the host product may be used—or caused to be used—by a patient or practitioner.

At step 760, the patient or practitioner may withdraw from the clinical trial and return the host product to the clinic. On the host product's return, the clinic may analyze the product label 100 (as shown in FIGS. 1, 2A, and 2B) of the host product. Based on its analysis, the image capture and communication device determines a type and one or more features for each of the one or more authentication elements, monitors, and/or identification elements, as shown at step 765.

At step 770, the image capture and communication device may access the one or more host servers 190 (as shown in FIG. 1). Once the image capture and communication device is either directly or indirectly connected to the host server, the image capture and communication device may transmit the type and features for each of one or more authentication elements, monitors, and/or identification elements present on product label 100, as shown at step 775. The image capture and communication device may receive an acceptability report from host servers 190 (as shown in FIG. 1) based on the type and features for each of one or more authentication elements, monitors, and/or identification elements present on product label 100, as shown at step 780. In addition, the acceptability report may also take into account historical information about the host product, including the data collected at the site of manufacture, inbound and outbound at the clinic, and at the practitioner's office, patient's home, and/or other place the host product was administered to the patient. In a further embodiment, any data collected by any image capture and communication devices from product label 100 may be taken into account as historical information for the product acceptability report. The image capture and communication device may receive the acceptability report from host servers 190 (as shown in FIG. 1) via SMS text message, TCP/IP messaging, email, FTP, PIN email, and/or instant message. In further embodiments, the image capture and communication device may receive the acceptability report from the host servers 190 (as shown in FIG. 1) by the host servers 190 providing a uniform resource locator (URL) to a website for the image capture and communication device to access through cellular network 180 (as shown in FIG. 1) or network 185 (as shown in FIG. 1). In such embodiments, host servers 190 (as shown in FIG. 1) post the acceptability report to the website available at the URL.

At step 785, the image capture and communication device may output the acceptability report. At step 795, based on the outputted acceptability report, either the user of the image capture and communication device—or the device itself—may determine whether the host product is acceptable for use. At step 796, if the host product is not acceptable for use, it may not be re-used and thus cannot be redistributed by the clinic or manufacturer and may be returned to the manufacturer for destruction. In a further embodiment, the acceptability report may include instructions transmitted or generated by the manufacturer about what the clinic should do with an unacceptable product. If the product is acceptable for use, at step 800, the host product may be returned to the manufacturer for restocking and/or repackaging. In a further embodiment, the acceptability report may include instructions transmitted or generated by the manufacturer about what the clinic should do with an acceptable product.

At step 805, on the host product's return, the manufacturer may analyze the product label 100 (as shown in FIGS. 1, 2A, and 2B) of the host product. Based on its analysis, the image capture and communication device determines a type and one or more features for each of the one or more authentication elements, monitors, and/or identification elements, as shown at step 810.

At step 815, the image capture and communication device may access the one or more host servers 190 (as shown in FIG. 1). Once the image capture and communication device is either directly or indirectly connected to the host server, the image capture and communication device may transmit the type and features for each of one or more authentication elements, monitors, and/or identification elements present on product label 100, as shown at step 820. The image capture and communication device may receive an acceptability report from host servers 190 (as shown in FIG. 1) based on the type and features for each of one or more authentication elements, monitors, and/or identification elements present on product label 100, as shown at step 825. In addition, the acceptability report may also take into account historical information about the host product, including the data collected at the site of manufacture, inbound and outbound at the clinic, and at the practitioner's office, patient's home, and/or other place the host product was administered to the patient. In a further embodiment, any data collected by any image capture and communication devices from product label 100 may be taken into account as historical information for the product acceptability report. The image capture and communication device may receive the acceptability report from host servers 190 (as shown in FIG. 1) via SMS text message, TCP/IP messaging, email, FTP, PIN email, and/or instant message. In further embodiments, the image capture and communication device may receive the acceptability report from the host servers 190 (as shown in FIG. 1) by the host servers 190 providing a uniform resource locator (URL) to a website for the image capture and communication device to access through cellular network 180 (as shown in FIG. 1) or network 185 (as shown in FIG. 1). In such embodiments, host servers 190 (as shown in FIG. 1) post the acceptability report to the website available at the URL.

At step 830, the image capture and communication device may output the acceptability report. At step 835, based on the outputted acceptability report, either the user of the image capture and communication device—or the device itself—may determine whether the host product is acceptable for use. At step 836, if the host product is not acceptable for use, it may not be re-stocked or repackaged and may be sent for destruction. In a further embodiment, the acceptability report may include instructions transmitted or generated by the manufacturer about what the manufacturer should do with an unacceptable product. If the product is acceptable for use, at step 840, the host product may be restocked, repackaged, and/or re-issued to a clinic and/or patient or practitioner In steps 600-840, the one or more image capture and communication devices may be the same image capture and communication devices, different image capture and communication devices, or the same device for some steps and different devices for other steps.

As shown in FIGS. 7A, 7B, 7C, 7D, 7E and 7F, according to one embodiment of the present invention a manufacturer of a host product may use systems and methods of the present invention to track the acceptability of the host product throughout the steps of its supply or distribution chain for the host product. For example, at step 900, the manufacturer may associate one or more host products with a product label 100 (as shown in FIGS. 1, 2A, and 2B) including at least two of one or more monitors, product identification elements, and authentication elements. During the association (at step 900), the manufacturer may set the limits or other data for each of the one or more monitors, product identification elements, and/or authentication elements; or, the manufacturer may use one or more monitors, product identification elements, and/or authentication elements with pre-set limits and/or data as appropriate for the particular host product.

At step 904, before the manufacturer is ready to release the product for distribution through its supply chain, an image capture and communication device may analyze a product label 100 (as shown in FIGS. 1, 2A, and 2B) of a host product at the host product's site of manufacture. Based on its analysis, for example, by scanning for visual or electronic signals indicative of one or more authentication elements, monitors, and/or identification elements present on product label 100, the image capture and communication device determines a type and one or more features for each of the one or more authentication elements, monitors, and/or identification elements, as shown at step 905.

At step 910, the image capture and communication device may access the one or more host servers 190 (as shown in FIG. 1). The image capture and communication device may accomplish such access by connecting to host servers 190 through network 185 (as shown in FIG. 1) and/or cellular network 180 (as shown in FIG. 1). In other embodiments, the image capture and communication device may connect to host servers 190 through a direct satellite link. Once the image capture and communication device is either directly or indirectly connected to the host server, the image capture and communication device may transmit the type and features for each of one or more authentication elements, monitors, and/or identification elements present on product label 100, as shown at step 915.

In one embodiment, the image capture and communication device may transmit the type and features to the host servers 190 (as shown in FIG. 1) via short message service (SMS) text message, TCP/IP messaging, email, FTP, PIN email, and/or instant message. The image capture and communication device may receive an acceptability report from host servers 190 (as shown in FIG. 1) based on the type and features for each of one or more authentication elements, monitors, and/or identification elements present on product label 100, as shown at step 920. The image capture and communication device may receive the acceptability report from host servers 190 (as shown in FIG. 1) via SMS text message, TCP/IP messaging, email, FTP, PIN email, and/or instant message. In further embodiments, the image capture and communication device may receive the acceptability report from the host servers 190 (as shown in FIG. 1) by the host servers 190 providing a uniform resource locator (URL) to a website for the image capture and communication device to access through cellular network 180 (as shown in FIG. 1) or network 185 (as shown in FIG. 1). In such embodiments, host servers 190 (as shown in FIG. 1) post the acceptability report to the website available at the URL.

At step 925, according to one embodiment of the present invention, the image capture and communication device may output the acceptability report. For example, image capture and communication devices 170, 160, and/or 110 may output a text-based and/or graphical-based acceptability report on display devices such as a LCD display, LED display, or CRT display. In addition, an audible report may be output in lieu of—or in addition to—the graphically displayed report. At step 930, based on the outputted acceptability report, either the user of the image capture and communication device—or the device itself—may determine whether the host product is acceptable for use. For example, the acceptability report may actually state "it is not acceptable for distribution" or "it is acceptable for distribution" or provide certain data for interpretation by its user or the device/host servers itself/themselves. At step 931, if the host product is not acceptable for use, it may not be shipped out. In a further embodiment, the acceptability report may include instructions transmitted or generated by the manufacturer about what the user should do with an unacceptable product. If the product is acceptable for use, at step 935, the host product is released to a supply chain intermediary user, such as a distributor or wholesaler.

At step 940, the clinic and/or delivery driver may analyze the inbound product label 100 (as shown in FIGS. 1, 2A, and 2B) of the host product at the clinic. Based on its analysis, the image capture and communication device determines a type and one or more features for each of the one or more authentication elements, monitors, and/or identification elements, as shown at step 945.

At step 950, the image capture and communication device may access the one or more host servers 190 (as shown in FIG. 1). Once the image capture and communication device is either directly or indirectly connected to the host server, the image capture and communication device may transmit the type and features for each of one or more authentication elements, monitors, and/or identification elements present on product label 100, as shown at step 955. The image capture and communication device may receive an acceptability report from host servers 190 (as shown in FIG. 1) based on the type and features for each of one or more authentication elements, monitors, and/or identification elements present on product label 100, as shown at step 960. In addition, the acceptability report may also take into account historical information about the host product, including the data collected at the site of manufacture. The image capture and communication device may receive the acceptability report from host servers 190 (as shown in FIG. 1) via SMS text message, TCP/IP messaging, email, FTP, PIN email, and/or instant message. In further embodiments, the image capture and communication device may receive the acceptability report from the host servers 190 (as shown in FIG. 1) by the host servers 190 providing a uniform resource locator (URL) to a web site for the image capture and communication device to access through cellular network 180 (as shown in FIG. 1) or network 185 (as shown in FIG. 1). In such embodiments, host servers 190 (as shown in FIG. 1) post the acceptability report to the website available at the URL.

At step 965, the image capture and communication device may output the acceptability report. At step 970, based on the outputted acceptability report, either the user of the image capture and communication device—or the device itself—may determine whether the host product is acceptable for use. At step 971, if the host product is not acceptable for use, it may cease the supply chain process (for example, not further distribute the host product) and return it to the manufacturer. In a further embodiment, the acceptability report may include instructions transmitted or generated by the manufacturer about what the supply chain intermediary user should do with an unacceptable product. If the product is acceptable for use, at step 975, the host product may be stored until such time as the supply chain intermediary user decides to release the host product to an end-user.

At step 980, the supply chain intermediary user may analyze the product label 100 (as shown in FIGS. 1, 2A, and 2B) of the stored host product. Based on its analysis, the image capture and communication device determines a type and one or more features for each of the one or more authentication elements, monitors, and/or identification elements, as shown at step 985.

At step 990, the image capture and communication device may access the one or more host servers 190 (as shown in FIG. 1). Once the image capture and communication device is either directly or indirectly connected to the host server, the image capture and communication device may transmit the type and features for each of one or more authentication elements, monitors, and/or identification elements present on product label 100, as shown at step 995. The image capture and communication device may receive an acceptability report from host servers 190 (as shown in FIG. 1) based on the type and features for each of one or more authentication elements, monitors, and/or identification elements present on product label 100, as shown at step 1000. In addition, the acceptability report may also take into account historical information about the host product, including the data collected at the site of manufacture and inbound at the supply chain intermediary user. The image capture and communication device may receive the acceptability report from host servers 190 (as shown in FIG. 1) via SMS text message, TCP/IP messaging, email, FTP, PIN email, and/or instant message. In further embodiments, the image capture and communication device may receive the acceptability report from the host servers 190 (as shown in FIG. 1) by the host servers 190 providing a uniform resource locator (URL) to a website for the image capture and communication device to access through cellular network 180 (as shown in FIG. 1) or network 185 (as shown in FIG. 1). In such embodiments, host servers 190 (as shown in FIG. 1) post the acceptability report to the website available at the URL.

At step 1005, the image capture and communication device may output the acceptability report. At step 1010, based on the outputted acceptability report, either the user of the image capture and communication device—or the device itself—may determine whether the host product is acceptable for use. At step 1011, if the host product is not acceptable for use, it may not be distributed to an end-user and is returned to the manufacturer. In a further embodiment, the acceptability report may include instructions transmitted or generated by the manufacturer about what the supply chain intermediary user should do with an unacceptable product. If the product is acceptable for use, at step 1015, the host product may be distributed to an end-user.

At step 1020, the end-user may analyze the product label 100 (as shown in FIGS. 1, 2A, and 2B) of the host product. Based on its analysis, the image capture and communication device determines a type and one or more features for each of the one or more authentication elements, monitors, and/or identification elements, as shown at step 1025.

At step 1030, the image capture and communication device may access the one or more host servers 190 (as shown in FIG. 1). Once the image capture and communication device is either directly or indirectly connected to the host server, the image capture and communication device may transmit the type and features for each of one or more authentication elements, monitors, and/or identification elements present on product label 100, as shown at step 1035. The image capture and communication device may receive an acceptability report from host servers 190 (as shown in FIG. 1) based on the type and features for each of one or more authentication elements, monitors, and/or identification elements present on product label 100, as shown at step 1040. In addition, the acceptability report may also take into account historical information about the host product, including the data collected at the site of manufacture and inbound and outbound at the supply chain intermediary user's location. The image capture and communication device may receive the acceptability report from host servers 190 (as shown in FIG. 1) via SMS text message, TCP/IP messaging, email, FTP, PIN email, and/or instant message. In further embodiments, the image capture and communication device may receive the acceptability report from the host servers 190 (as shown in FIG. 1) by the host servers 190 providing a uniform resource locator (URL) to a web site for the image capture and communication device to access through cellular network 180 (as shown in FIG. 1) or network 185 (as shown in FIG. 1). In such embodiments, host servers 190 (as shown in FIG. 1) post the acceptability report to the website available at the URL.

At step 1045, the image capture and communication device may output the acceptability report. At step 1050, based on the outputted acceptability report, either the user of the image capture and communication device—or the device itself—may determine whether the host product is acceptable for use. At step 1051, if the host product is not acceptable for use, it may not be used or caused to be used by the end-user and is returned to the manufacturer directly or indirectly through the supply chain intermediary user. In a further embodiment, the acceptability report may include instructions transmitted or generated by the manufacturer about what the end-user should do with an unacceptable product. If the product is acceptable for use, at step 1055, the host product may be used—or caused to be used—by the end-user.

At step 1060, the end-user may decide to return the host product to the supply chain intermediary user or the manufacturer. On the host products return to the supply chain intermediary user, the supply chain intermediary user may analyze the product label 100 (as shown in FIGS. 1, 2A, and 2B) of the host product. Based on its analysis, the image capture and communication device determines a type and one or more features for each of the one or more authentication elements, monitors, and/or identification elements, as shown at step 1065.

At step 1070, the image capture and communication device may access the one or more host servers 190 (as shown in FIG. 1). Once the image capture and communication device is either directly or indirectly connected to the host server, the image capture and communication device may transmit the type and features for each of one or more authentication elements, monitors, and/or identification elements present on product label 100, as shown at step 1075. The image capture and communication device may receive an acceptability report from host servers 190 (as shown in FIG. 1) based on the type and features for each of one or more authentication elements, monitors, and/or identification elements present on product label 100, as shown at step 1080.

In addition, the acceptability report may also take into account historical information about the host product, including the data collected at the site of manufacture, inbound and outbound at the supply chain intermediary user's location, and at the end-user's location or place it used the host product. In a further embodiment, any data collected by any image capture and communication devices from product label 100 may be taken into account as historical information for the product acceptability report. The image capture and communication device may receive the acceptability report from host servers 190 (as shown in FIG. 1) via SMS text message, TCP/IP messaging, email, FTP, PIN email, and/or instant message. In further embodiments, the image capture and communication device may receive the acceptability report from the host servers 190 (as shown in FIG. 1) by the host servers 190 providing a uniform resource locator (URL) to a website for the image capture and communication device to access through cellular network 180 (as shown in FIG. 1) or network 185 (as shown in FIG. 1). In such embodiments, host servers 190 (as shown in FIG. 1) post the acceptability report to the website available at the URL.

At step 1085, the image capture and communication device may output the acceptability report. At step 1090, based on the outputted acceptability report, either the user of the image capture and communication device—or the device itself—may determine whether the host product is acceptable for use. At step 1091, if the host product is not acceptable for use, it may not be re-used and thus cannot be redistributed by the clinic or manufacturer and may be returned to the manufacturer for destruction. In a further embodiment, the acceptability report may include instructions transmitted or generated by the manufacturer about what the supply chain intermediary user should do with an unacceptable product. If the product is acceptable for use, at step 1095, the host product may be returned to the manufacturer for restocking and/or repackaging. In a further embodiment, the acceptability report may include instructions transmitted or generated by the manufacturer about what the supply chain intermediary user should do with an acceptable product.

At step 1100, on the host product's return, the manufacturer may analyze the product label 100 (as shown in FIGS. 1, 2A, and 2B) of the host product. Based on its analysis, the image capture and communication device determines a type and one or more features for each of the one or more authentication elements, monitors, and/or identification elements, as shown at step 1105.

At step 1110, the image capture and communication device may access the one or more host servers 190 (as shown in FIG. 1). Once the image capture and communication device is either directly or indirectly connected to the host server, the image capture and communication device may transmit the type and features for each of one or more authentication elements, monitors, and/or identification elements present on product label 100, as shown at step 1115. The image capture and communication device may receive an acceptability report from host servers 190 (as shown in FIG. 1) based on the type and features for each of one or more authentication elements, monitors, and/or identification elements present on product label 100, as shown at step 1120. In addition, the acceptability report may also take into account historical information about the host product, including the data collected at the site of manufacture, inbound and outbound at the supply chain intermediary user's location, and at the end-user location or place the end-user used the host product.

In a further embodiment, any data collected by any image capture and communication devices from product label 100 may be taken into account as historical information for the product acceptability report. The image capture and communication device may receive the acceptability report from host servers 190 (as shown in FIG. 1) via SMS text message, TCP/IP messaging, email, FTP, PIN email, and/or instant message. In further embodiments, the image capture and communication device may receive the acceptability report from the host servers 190 (as shown in FIG. 1) by the host servers 190 providing a uniform resource locator (URL) to a website for the image capture and communication device to access through cellular network 180 (as shown in FIG. 1)

or network 185 (as shown in FIG. 1). In such embodiments, host servers 190 (as shown in FIG. 1) post the acceptability report to the website available at the URL.

At step 1125, the image capture and communication device may output the acceptability report. At step 1130, based on the outputted acceptability report, either the user of the image capture and communication device—or the device itself—may determine whether the host product is acceptable for use. At step 1131, if the host product is not acceptable for use, it may not be re-stocked or repackaged and may be sent for destruction. In a further embodiment, the acceptability report may include instructions transmitted or generated by the manufacturer about what the manufacturer should do with an unacceptable product. If the product is acceptable for use, at step 1135, the host product may be restocked, repackaged, and/or re-issued to a supply chain intermediary user and/or end-user.

In steps 900-1135, the one or more image capture and communication devices may be the same image capture and communication devices, different image capture and communication devices, or the same device for some steps and different devices for other steps. In one embodiment, a mobile device or a host server can correlate information from an environmental monitor with known product item history information, for example, distribution information, an e-pedigree, and/or environmental monitor information from other comparable product items, to evaluate credibility of the environmental monitor information, and use the evaluation to help determine authenticity. The outcome can be included in the acceptability report.

In one embodiment, the invention includes providing an image capture and communication device with contact information or security tokens or information to permit secure communication with an authentic supplier-approved host server and, optionally, to prevent security breaches or to prevent communication with a counterfeit or unsecured host server. For example, authentic supplier contact information or security features can be embedded in the software application installed on the image capture and communication device for imaging labels and processing the image data.

In one embodiment, the invention relates to software modules or executable code configured to transmit high resolution images of a product label and/or individual label elements to host server. In one embodiment, a resolution-reducing procedure, such as a compression scheme used to reduce image file size is overridden or by-passed, if such a procedure is used by the device for remote communication. With high resolution data thus preserved, software modules such as automated image data filters can process a high resolution image received at a remote site to effectively magnify the image, or localize areas of the image that contain pixels of interest, such as the pixels that constitute the patterned region of a bar code or the colored pixels indicative of monitor state for an environmental monitor. In turn, the software can be configured to automatically interpret elements not visible to normal human inspection of a product label. This interpretation can verify authenticity, for example, by reading microtext, or other information not readily apparent to a human viewer unaided by special viewing equipment, such as a microscope, can determine color changes in a monitor that can be compared to a database of optical values, or can convert a barcode into the data it contains or to links to or in a database.

In one embodiment, the invention relates to executable code or software modules that can generate a viewing frame to frame a product label area or areas to be captured, optionally with cooperative markings on the label. This process or method can include providing a viewing frame geometrically adapted, along with an appropriate user instruction, to cause the image to be captured while viewed at a particular viewing angle, optionally with two or more such viewing frames providing two or more viewing angles. These viewing angles allow for imaging an optically variable device such as an authentication element or a portion of same, from different perspectives to facilitate reading the optically variable device. Accordingly, by obtaining multiple frames of image data the software can selectively ignore unwanted frames or analyze a common feature, such as an authentication element, across multiple image data sets. The executable code can include user instructions to position the viewed image in relation to the viewing frame so that the viewed image is positioned at a predetermined distance from the image capture and communication device for image capture, if desired, optionally with a predetermined orientation, such as parallel to the label, or another positioning parameter.

Additional Computer and Mobile Device Based Embodiment Details

The present invention may be embodied in many different forms, including, but in no way limited to, computer program logic for use with a processor (e.g., a microprocessor, microcontroller, digital signal processor, or general purpose computer), programmable logic for use with a programmable logic device, (e.g., a Field Programmable Gate Array (FPGA) or other PLD), discrete components, integrated circuitry (e.g., an Application Specific Integrated Circuit (ASIC)), or any other means including any combination thereof.

In one embodiment of the invention, some or all of the image data and subsets thereof are processed and transformed using a set of computer program instructions or software instructions that is converted into a computer executable form, stored as such in a computer readable medium, and executed by a microprocessor under the control of an operating system. In one embodiment, image data obtained from a label is transformed into processor-understandable instructions suitable for generating an acceptability report, or for routing the results of identifying and reading the label elements to one or more data managements systems.

Computer program logic implementing all or part of the functionality previously described herein may be embodied in various forms, including, but in no way limited to, a source code form, a computer executable form, and various intermediate forms (e.g., forms generated by an assembler, compiler, linker, or locator). Source code may include a series of computer program instructions implemented in any of various programming languages (e.g., an object code, an assembly language, or a high-level language such as Fortran, Open GL, GPU instruction sets, C, C++, C#, JAVA, or HTML) for use with various operating systems or operating environments.

The source code may define and use various data structures, methods, and instructions relating to or suitable for implementing the invention embodiments described herein including optical compensation, product label and non-product label correlation and data routing, image data capture and processing, authentication, environmental monitor detection and reading and various other invention features described herein. The source code may be in a computer executable form (e.g., via an interpreter), or the source code may be converted (e.g., via a translator, an assembler, or a compiler) into a computer executable form.

The computer program may be fixed in any form (e.g., source code form, computer executable form, or an intermediate form) either permanently or transitorily in a tangible storage medium, such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), a PC card (e.g., PCMCIA card), or other memory device.

The computer program may be fixed in any form in a signal that is transmittable to a computer using any of various communication technologies, including, but in no way limited to, analog technologies, digital technologies, optical technologies, wireless technologies, networking technologies, and internetworking technologies. The computer program may be distributed in any form such as stored in a removable storage medium with accompanying printed or electronic documentation (e.g., shrink-wrapped software), or preloaded with a computer system (e.g., on system ROM or fixed disk), or distributed over a network.

Programmable logic may be fixed either permanently or transitorily in a tangible storage medium, such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), or other memory device. The programmable logic may be fixed in a signal that is transmittable to a computer using any of various communication technologies, including, but in no way limited to, analog technologies, digital technologies, optical technologies, wireless technologies (e.g., Bluetooth), networking technologies, and internet technologies. The programmable logic may be distributed stored on a removable storage medium with accompanying printed or electronic documentation (e.g., shrink-wrapped software), preloaded with a computer system (e.g., on system ROM or fixed disk), or distributed from a server or electronic bulletin board over the communication system (e.g., the Internet or World Wide Web).

Various examples of suitable processing modules are discussed below in more detail. As used herein a module or software module refers to software, hardware, or firmware suitable for performing a specific data processing, data transmission task or other automated function or process using a processor or computer. In one embodiment a module or software module refers to a software routine, program, or other memory resident application suitable for performing one or more of the methods, steps, or processing or using image data, frames of data, or subsets of the foregoing described herein or otherwise relating to the embodiments of the invention.

In addition, mobile devices having graphic processors can be configured such that image processing is performed using the graphic processor to expedite analysis of a given label. Alternatively, if the mobile device lacks sufficient processing power or if a large number of labels are being processed, or for another reason, a compressed version of the image data can be relayed to a remote server such as a host server for processing of the image data. In turn, an acceptability report or other data derived from the image data can then be returned to the mobile device by the server.

In one embodiment, an image capture and communication device is programmed with, or otherwise has, one or more executable software applications installed thereon, or accessible therefrom, that exchange label data, patient data, entity data, image data, and/or other types of data with a detection process software module, optical compensation software module, report generating software module, data processing software module, user interface software module, scripting instruction software module, other software modules and/or one or more host servers.

Computers and computer systems described herein may include operatively associated computer-readable media such as memory for storing software applications, or instruction sets, used in obtaining, processing, storing and/or communicating data. Such memory can be internal, external, remote or local with respect to its operatively associated computer or computer system.

Memory may also include any means for storing software or other instructions including, for example and without limitation, a hard disk, an optical disk, floppy disk, DVD (digital versatile disc), CD (compact disc), memory stick, flash memory, ROM (read only memory), RAM (random access memory), DRAM (dynamic random access memory), PROM (programmable ROM), EEPROM (extended erasable PROM), and/or other like computer-readable media.

In general, computer-readable memory media applied in association with embodiments of the invention described herein may include any memory medium capable of storing instructions executed by a programmable apparatus. Where applicable, method steps described herein may be embodied or executed as instructions stored on a computer-readable memory medium or memory media.

It is to be understood that the figures and descriptions of the invention have been simplified to illustrate elements that are relevant for a clear understanding of the invention, while eliminating, for purposes of clarity, other elements. Those of ordinary skill in the art will recognize, however, that these and other elements may be desirable. However, because such elements are well known in the art, and because they do not facilitate a better understanding of the invention, a discussion of such elements is not provided herein. It should be appreciated that the figures are presented for illustrative purposes and not as construction drawings. Omitted details and modifications or alternative embodiments are within the purview of persons of ordinary skill in the art.

It can be appreciated that, in certain embodiments of the invention, a single component may be replaced by multiple components, and multiple components may be replaced by a single component, to provide an element or structure or to perform a given function or functions. Except where such substitution would not be operative to practice certain embodiments of the invention, such substitution is considered within the scope of the invention.

The examples presented herein are intended to illustrate potential and specific implementations of the invention. It can be appreciated that the examples are intended primarily for purposes of illustration of the invention for those skilled in the art. There may be variations to these diagrams or the operations described herein without departing from the spirit of the invention. For instance, in certain cases, method steps or operations may be performed or executed in differing order, or operations may be added, deleted or modified.

Furthermore, whereas particular embodiments of the invention have been described herein for the purpose of illustrating the invention and not for the purpose of limiting the same, it will be appreciated by those of ordinary skill in the art that numerous variations of the details, materials and arrangement of elements, steps, structures, and/or parts may be made within the principle and scope of the invention without departing from the invention as described in the claims.

The embodiments, embodiments, features, and examples of the invention are to be considered illustrative in all respects and are not intended to limit the invention, the scope of which is defined only by the claims. Other embodiments, modifications, and usages will be apparent to those skilled in the art without departing from the spirit and scope of the claimed invention.

The use of headings and sections in the application is not meant to limit the invention; each section can apply to any embodiment, embodiment, or feature of the invention.

Throughout the application, where systems or devices are described as having, including, or comprising specific components, or where processes are described as having, including or comprising specific process steps, it is contemplated that systems or devices of the invention can also consist essentially of, or consist of, the recited components, and that the processes of the present teachings also consist essentially of, or consist of, the recited process steps.

In the application, where an element or component is said to be included in and/or selected from a list of recited elements or components, it should be understood that the element or component can be any one of the recited elements or components and can be selected from a group consisting of two or more of the recited elements or components. Further, it should be understood that elements and/or features of a composition, an apparatus, or a method described herein can be combined in a variety of ways without departing from the spirit and scope of the present teachings, whether explicit or implicit herein.

The use of the terms "include," "includes," "including," "have," "has," or "having" should be generally understood as open-ended and non-limiting unless specifically stated otherwise.

The use of the singular herein includes the plural (and vice versa) unless specifically stated otherwise. Moreover, the singular forms "a," "an," and "the" include plural forms unless the context clearly dictates otherwise. In addition, where the use of the term "about" is before a quantitative value, the present teachings also include the specific quantitative value itself, unless specifically stated otherwise.

It should be understood that the order of steps or order for performing certain actions is immaterial so long as the present teachings remain operable. Moreover, two or more steps or actions may be conducted simultaneously.

Where a range or list of values is provided, each intervening value between the upper and lower limits of that range or list of values is individually contemplated and is encompassed within the invention as if each value were specifically enumerated herein. In addition, smaller ranges between and including the upper and lower limits of a given range are contemplated and encompassed within the invention. The listing of exemplary values or ranges is not a disclaimer of other values or ranges between and including the upper and lower limits of a given range.

Although illustrative embodiments have been shown and described herein in detail, it should be noted and will be appreciated by those skilled in the art that there may be numerous variations and other embodiments that may be equivalent to those explicitly shown and described. For example, the scope of the present invention is not necessarily limited in all cases to execution of the aforementioned steps in the order discussed. Unless otherwise specifically stated, terms and expressions have been used herein as terms of description, not of limitation. Accordingly, the invention is not to be limited by the specific illustrated and described embodiments (or the terms or expressions used to describe them) but only by the scope of claims.

What is claimed is:

1. An apparatus for processing a product provided with a product label, the apparatus comprising:
   a memory; and
   a processor in communication with the memory; and
   a camera in communication with the processor and the memory, wherein the memory comprises instructions executable by the processor to cause the processor to:
   capture using a camera, first image data from a product label, wherein the product label comprises an environmental monitor having a first shape and an environmental monitor state, the first image data being captured from multiple angles using the camera;
   receive the first image data from the camera;
   detect the presence and position of the first shape from the first image data captured from multiple angles;
   in response to detecting the presence and position of the first shape, process the first image data captured from multiple angles to identify, based on the position of the first shape, a first subset of the first image data captured from multiple angles obtained from the environmental monitor;
   determine the environmental monitor state from the first subset of the first image data captured from multiple angles; and
   generate a product acceptability report based upon the determined monitor state.

2. The apparatus of claim 1 wherein the memory and processor are disposed in a mobile device.

3. The apparatus of claim 1 wherein the memory further comprises instructions that when executed by the processor cause the processor to automatically compensate for noise or glare in the first image data.

4. The apparatus of claim 1 further comprising a display in electrical communication with the processor and wherein the memory device further comprises instructions that when executed by the processor cause the processor to inform a user, using the display, to capture the first image data from multiple angles.

5. The apparatus of claim 1 wherein the environmental monitor experiences a detectable change in color when exposed to an environmental stimulus damaging to the product, and wherein determining the environmental monitor state includes detecting whether the detectable change in color has occurred.

6. The apparatus of claim 1, wherein the memory further comprises instructions executable by the processor to cause the processor to:
   capture using the camera, second image data;
   identify a patterned region in the second image data;
   process the second image data in response to identifying the patterned region to identify a second subset of the second image data containing a first identifier; and
   determine a source of the first identifier, wherein the acceptability report is further based on information relating to the determined source.

7. The apparatus of claim 6 wherein the instructions further cause the processor to
   process a third subset of the second image data to determine an authentication state; and wherein
   the acceptability report indicates that the product is acceptable conditioned on whether the determined environmental monitor state satisfies a predetermined acceptance level and the authentication state is verified as authentic.

8. The apparatus of claim 7, wherein the second image data contains entity information, and wherein the memory further comprises instructions that when executed by the processor cause the processor to:
  route the monitor state, the authentication state, and the entity information to a database.

9. The apparatus of claim 8 wherein the entity is selected from the group consisting of: a patient; a product transport company; a clinical trial administrator; a hospital; a pharmaceutical company; a supplier; a distributor; a quality control service provider; a manufacturer; and a consumer.

10. The apparatus of claim 8, wherein the memory further comprises instructions executable by the processor to populate a records management system with event data associated with an event relating to a product associated with the product label.

11. The apparatus of claim 10, wherein the event is selected from the group consisting of:
  vaccination of the entity with the product,
  delivery of the product to the entity,
  performing a procedure on the entity,
  rejection of the product by the entity,
  consumption of the product by the entity,
  acknowledgement of the acceptability report by the entity,
  the entity performing an experiment using the product, and
  combinations of two or more of the foregoing events.

12. The apparatus of claim 1, wherein apparatus is a mobile device comprising a display and the camera.

13. The apparatus of claim 1, wherein the memory further comprises instructions executable by the processor to prevent the captured first image data from being pre-processed after the image is captured by the camera by controlling an application programming interface used to control the camera.

14. The apparatus of claim 1, wherein the first image data comprises a plurality of frames of image data and wherein the memory further comprises instructions executable by the processor to differentiate between the plurality of frames and remove optical defects based on the differences between the plurality of frames.

15. The apparatus of claim 1, wherein the memory further comprises instructions executable by the processor to adjust a dynamic range for the first image data using a patterned region as a reference, the patterned region comprising a black and white barcode.

16. The apparatus of claim 1, wherein the memory further comprises instructions executable by the processor to identify the first subset of image data based on the first image data captured from the plurality of angles.

17. The apparatus of claim 1, wherein the product label is configured for use with a product that requires cold storage, but that can be exposed to an ambient room temperature for a predetermined time period such that the monitor state undergoes a change detectable in the first image data if the predetermined time period is exceeded, and wherein the memory further comprises instructions executable by the processor to determine from the monitor state that the predetermined time period for exposure to the ambient room temperature has not been exceeded.

18. The apparatus of claim 17, wherein the memory further comprises instructions executable by the processor to determine a first optical density value correlated with the environmental monitor state and comparing the first optical density value with a plurality of optical densities correlated with residual shelf lives of the product.

19. The apparatus of claim 17, wherein the memory further comprises instructions executable by the processor to provide an estimated shelf life for the product in the acceptability report.

20. The apparatus of claim 1, wherein the first shape is approximately circular, wherein the memory further comprises instructions executable by the processor to identify a plurality of ellipses in the first image data, the ellipses in the first image data being images of the circular indicator on the label.

* * * * *